(12) United States Patent
Velazquez et al.

(10) Patent No.: US 8,187,339 B2
(45) Date of Patent: May 29, 2012

(54) FOAM HAIR COLORANT COMPOSITION

(75) Inventors: Jose Maria Velazquez, Ascot (GB); Sebastian Karol Galazka, Loveland, OH (US); Brandon Scott Lane, Hamilton, OH (US); Firoj Vohra, Mason, OH (US); Elizabeth H. Agostino, Loveland, OH (US); George Scott Kerr, Mason, OH (US); Robert Drennan Lewis, West Chester, OH (US); Christopher Gerald Donner, Liberty, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/972,312

(22) Filed: Dec. 17, 2010

(65) Prior Publication Data

US 2011/0284584 A1 Nov. 24, 2011

Related U.S. Application Data

(60) Provisional application No. 61/287,931, filed on Dec. 18, 2009.

(51) Int. Cl.
*A61Q 5/10* (2006.01)
(52) U.S. Cl. .............. 8/405; 8/406; 8/435; 8/477; 8/552
(58) Field of Classification Search .............. 8/405, 406, 8/435, 477, 552
See application file for complete search history.

(56) References Cited

U.S. PATENT DOCUMENTS

| | | | |
|---|---|---|---|
| 3,578,387 A | 5/1971 | Charles | |
| 3,709,437 A | 1/1973 | Wright | |
| 3,937,364 A | 2/1976 | Wright | |
| 3,977,826 A | 8/1976 | Iscowitz | |
| 4,022,351 A | 5/1977 | Wright | |
| 4,147,306 A | 4/1979 | Bennett | |
| 4,184,615 A | 1/1980 | Wright | |
| 4,615,467 A | 10/1986 | Grogan | |
| 4,796,812 A | 1/1989 | Grollier | |
| 4,921,170 A | 5/1990 | Grollier | |
| 5,443,569 A | 8/1995 | Uehira | |
| 6,106,578 A | 8/2000 | Jones | |
| 6,604,693 B2 | 8/2003 | Santagiuliana | |
| 6,835,210 B1 | 12/2004 | Bartolone | |
| 7,040,507 B2 * | 5/2006 | Koike et al. | 222/94 |
| 7,850,049 B2 | 12/2010 | Ciavarella | |
| 7,955,400 B2 | 6/2011 | Fujinuma | |
| 8,025,702 B2 | 9/2011 | Fujinuma | |

(Continued)

FOREIGN PATENT DOCUMENTS

EP    1 142 563 A1    10/2001

(Continued)

OTHER PUBLICATIONS

Leung, A Y, "Encyclopedia of Common Natural Ingredients Used in Food, Drugs and Cosmetics (2d Edition)", Jan. 1, 1996, Wiley, NY, US, p. 446.

*Primary Examiner* — Eisa Elhilo
(74) *Attorney, Agent, or Firm* — Carl J. Roof

(57) ABSTRACT

A hair colorant composition being essentially free of surfactant and having a specific perfume system for the hair colorant composition, where the hair colorant composition is capable of forming a foamed hair colorant composition.

34 Claims, 4 Drawing Sheets

U.S. PATENT DOCUMENTS

| | | |
|---|---|---|
| 8,025,703 B2 | 9/2011 | Ogawa |
| 2002/0058017 A1 | 5/2002 | Tajima |
| 2003/0180238 A1 | 9/2003 | Sakurai |
| 2003/0192133 A1 | 10/2003 | Matsuo |
| 2004/0213752 A1 | 10/2004 | Fujinuma |
| 2004/0254253 A1 | 12/2004 | Culeron |
| 2005/0222001 A1 | 10/2005 | Baumeister |
| 2005/0226824 A1 | 10/2005 | Kawa |
| 2006/0054634 A1 | 3/2006 | Mekata |
| 2006/0207037 A1 | 9/2006 | Fadel |
| 2006/0219738 A1 | 10/2006 | Ilzuka |
| 2008/0087293 A1 | 4/2008 | Glenn |
| 2010/0126522 A1 | 5/2010 | Fujinuma |
| 2010/0126523 A1 | 5/2010 | Fujinuma |
| 2010/0236570 A1 | 9/2010 | Fujinuma |
| 2010/0242187 A1 | 9/2010 | Miyabe |
| 2010/0251488 A1 | 10/2010 | Fujinuma |
| 2010/0257677 A1 | 10/2010 | Miyabe |
| 2010/0299848 A1 | 12/2010 | Fujinuma |
| 2010/0313905 A1 | 12/2010 | Fujinuma |
| 2010/0316583 A1 | 12/2010 | Fujinuma |
| 2011/0073128 A1 | 3/2011 | Ogawa |
| 2011/0214682 A1 | 9/2011 | Fujinuma |
| 2011/0284421 A1 | 11/2011 | Lane |
| 2011/0284586 A1 | 11/2011 | Kerr |
| 2011/0284587 A1 | 11/2011 | Galazka |

FOREIGN PATENT DOCUMENTS

| | | |
|---|---|---|
| FR | 2604622 | 12/1990 |
| JP | 2007-291015 A | 11/2007 |
| JP | 2007-291016 A | 11/2007 |
| JP | 2007-314523 A | 12/2007 |
| JP | 2007-314524 A | 12/2007 |
| JP | 2009-149322 A | 7/2009 |
| JP | 2009-149323 A | 7/2009 |
| JP | 2009-149324 A | 7/2009 |
| JP | 2009-149325 A | 7/2009 |
| JP | 2009-149326 A | 7/2009 |
| JP | 2009-149327 A | 7/2009 |
| JP | 2010-006804 A | 1/2010 |
| JP | 2010-006805 A | 1/2010 |
| WO | WO 91/14759 | 10/1991 |
| WO | WO 97/013585 | 4/1997 |
| WO | WO 2009/130461 | 10/2009 |
| WO | WO 2010/106789 | 9/2010 |

* cited by examiner

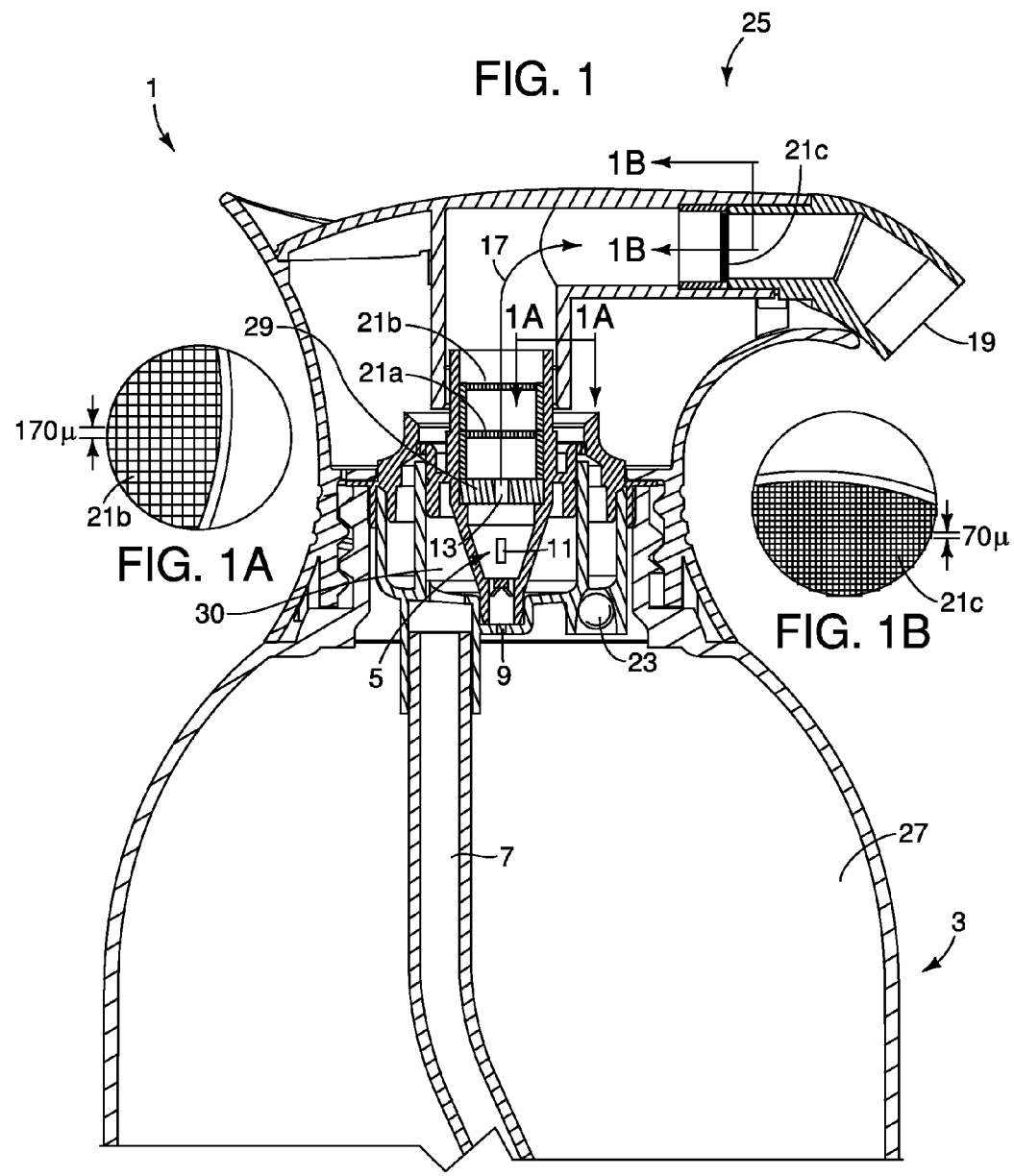

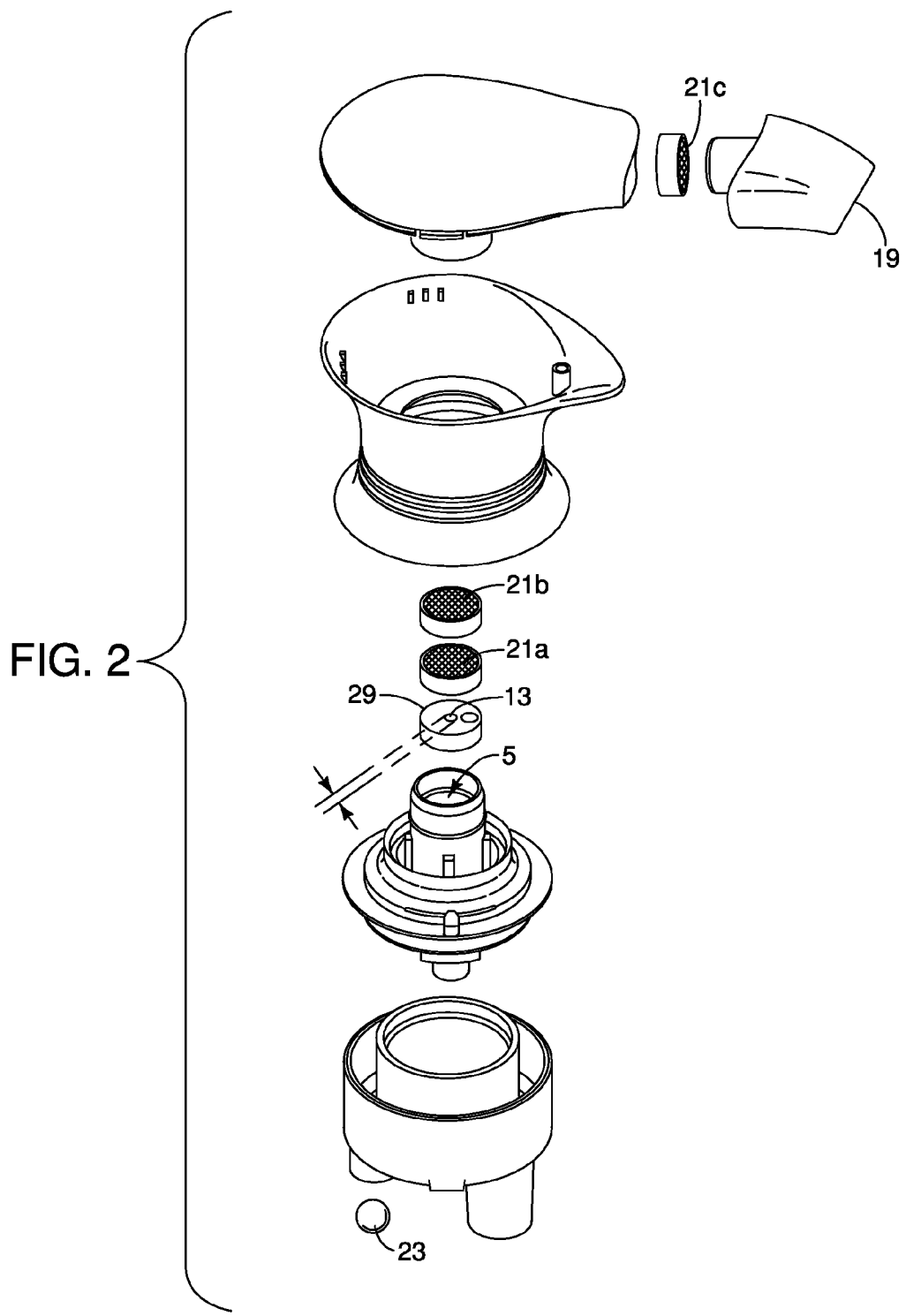

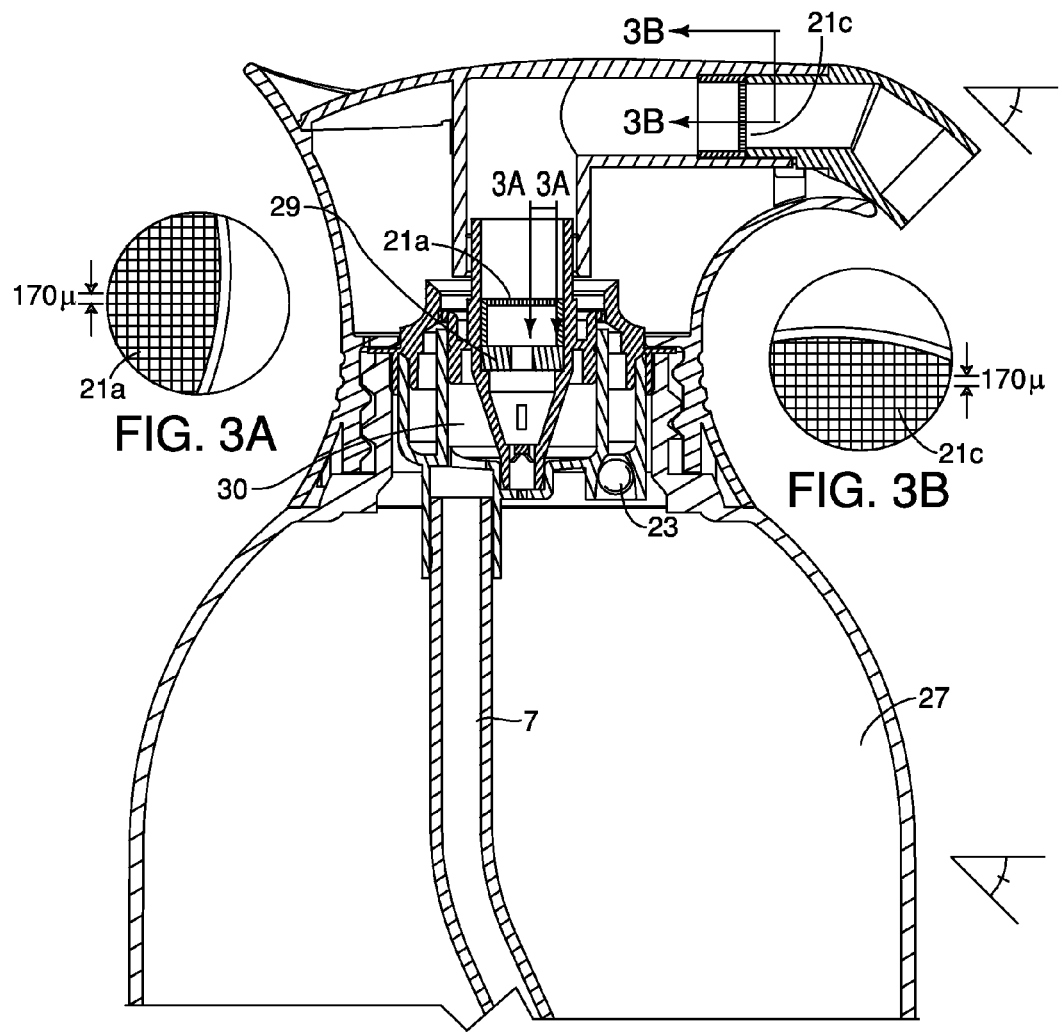

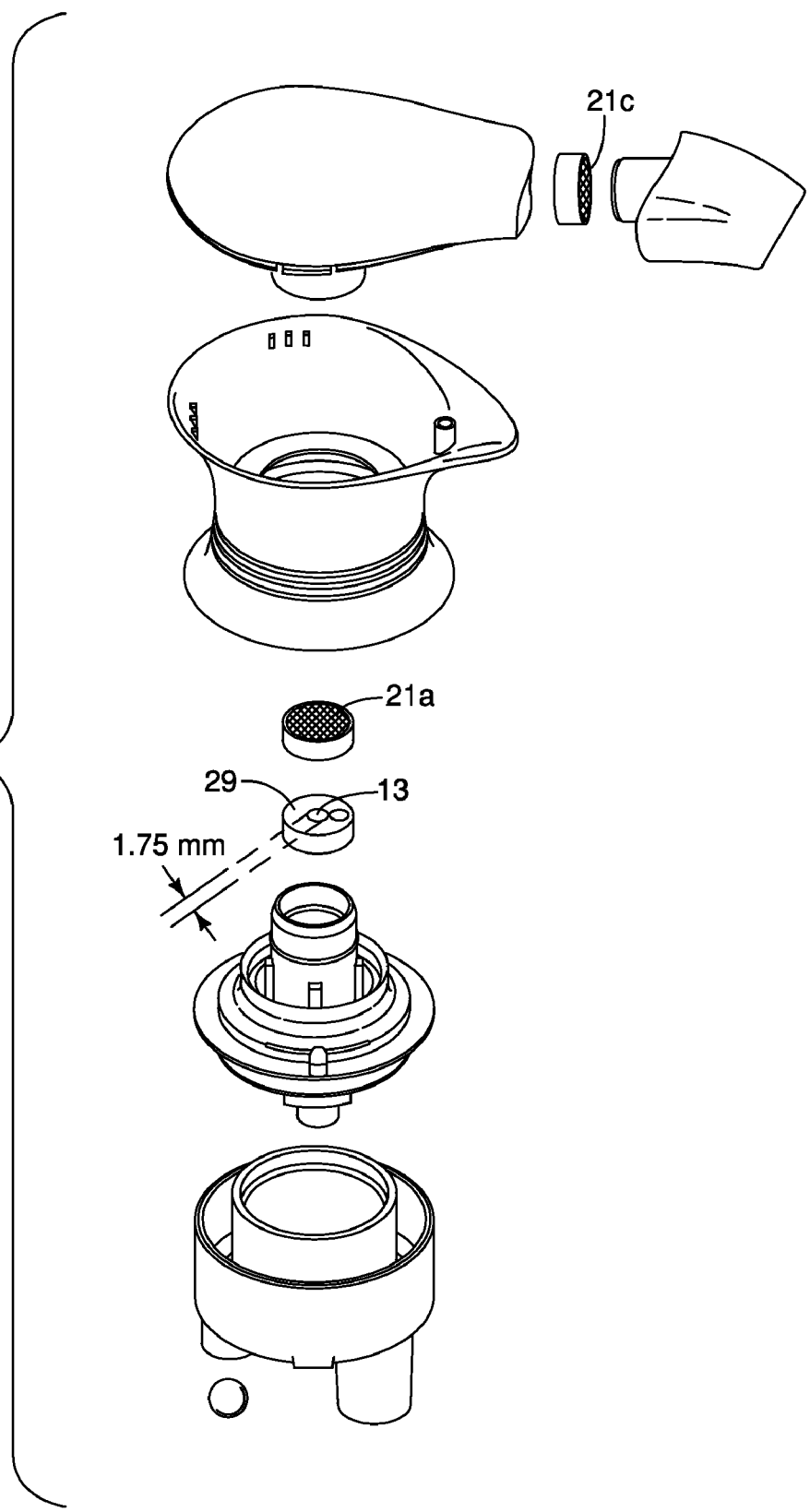

FOAM HAIR COLORANT COMPOSITION

CROSS REFERENCE TO RELATED APPLICATION

This application claims the benefit of U.S. Provisional Application Ser. No. 61/287,931 filed Dec. 18, 2009.

FIELD OF THE INVENTION

The present invention relates to a hair colorant composition essentially free of surfactant for use in combination with a foaming dispenser with a specific perfume system.

BACKGROUND OF THE INVENTION

An outstanding issue with respect to hair colorants includes ease of application and concerns over messy application resulting in skin staining and uneven hair color results. Recent trends indicate that consumers find handling of foamed products preferable to gels, creams or liquids.

Foamed products are known to be generated in one of two ways. The first being the use of a compressed gas (aerosols) which are admixed with a composition that is evacuated from a container by the consumer. A commercial example of this would be Kanebo Cosmetics's Simpro hair colorant. GB2188257A discusses a device for dispensing a two-component product, such as shampoos or dyes in a pressurized container and dispensed in the form of foam.

Outstanding issues with pressurized systems such as these examples are that oxidative hair colorants are radically initiated reactions that require sequestration from oxygen or segregation of the developer from the tint components (couplers, primaries, etc.) until use of the hair colorant is desired by the consumer. The sequestering packaging results in expensive, yet ineffective packaging for dispensing the hair colorant due the lack of control of the ratio of tint components to developer components coming out of the pressurized system or ineffective in segregating the hair colorant from oxygen.

The second way to generate a foam product is via a non-pressurized dispenser in the form of a pump foamer or squeeze foamer. A commercial example of a pump foamer would be Youngrace Bubble Hair Color product. A commercial example of a squeeze foamer would be Kao's Prettia Soft Foam Color, Liese Bubble Hair Color or Blaune Foam Color products. See also US 2004/0213752A1. Further, U.S. Pat. No. 7,040,507 discusses a foam-type hair dye apparatus for converting a liquid hair dye into foam.

Pump foamers can be difficult to utilize with oxidative hair colorant composition due to the use of metal parts, such as springs, that are exposed to the oxidative hair colorant composition. Due to the high pH of the dye composition subcomponent and presence of an oxidizing agent, the composition reacts with metal parts of the pump mechanism, such as springs, causing damage to the pump foamer and to the composition when oxidized metal ions contaminate the composition.

Therefore, it is a desire to provide an hair colorant product having a liquid hair colorant composition in a manually-actuable, non-aerosol dispenser. Further, there exists a further desire to minimize damage to hair when using hair coloring products while producing good end color results.

It has been found that the reduction or elimination of surfactants from the hair coloring composition can address the outstanding needs of such products and provide further desired benefits. However, a reduction of surfactants from the hair colorant composition cause most perfumes to be insoluble or unstable in the hair colorant compositions due to the hydrophobic nature of perfumes (being essentially oils). Additionally, perfumes may cause premature foam collapse than desired, leaving a liquid rather than a foam in a user's hand. It has been found that careful selection of perfume components via a ClogP criteria results in perfumes that are soluble and stable in the hair colorant composition which is essentially free of surfactants and do not cause foam instability or premature collapse of the foam.

SUMMARY OF THE INVENTION

According to one aspect of the invention there is provided a hair colorant product comprising an hair colorant composition contained in a manually-actuable, non-aerosol dispenser, the composition comprising a hair dye, an alkalizing agent, an oxidizing agent, a foam stabilizing agent which is a member selected from the group consisting of polymeric emulsifiers and polymeric foam stabilizers and mixtures thereof and a perfume comprising an Average ClogP less than 1.5, wherein the hair colorant composition is substantially free of surfactant and when dispensed from the manually-actuable, non-aerosol dispenser result is a foam comprising a specific foam volume from about 6 to about 14 ml/g, preferably from about 7.5 ml/g to about 12 ml/g, more preferably from about 8 to about 10.5 ml/g.

According to a further aspect of the present application is a hair colorant composition comprising: (i) a hair dye, (ii) an alkalizing agent, (iii) an oxidizing agent, (iv) a foam stabilizing agent which is a member selected from the group consisting of polymeric emulsifiers and polymeric foam stabilizers and mixtures thereof and (v) a perfume comprising a blend of perfume raw materials in which up to 30% by weight of the perfume consists essentially of perfume raw materials having a ClogP in the range 1.5 to 2.5 and the balance of the perfume consists essentially of perfume raw materials having a ClogP of less than 1.5, wherein the hair colorant composition is substantially free of surfactant.

According to a further aspect of the invention there is provided a kit comprising containing components to form an hair colorant composition the kit comprising: a tint composition component comprising a hair dye, an alkalizing agent and a perfume; wherein the perfume comprises an Average ClogP less than 1.5; a developer composition component comprising an oxidizing agent and a foam stabilizing agent which is a member selected from the group consisting of polymeric emulsifiers and polymeric foam stabilizers and mixtures thereof; a manually-actuable, non-aerosol dispenser, the dispenser capable of dispending the mixture of the tint composition component and developer composition component in a foam comprising a specific foam volume from about 6 to about 14 ml/g, preferably from about 7.5 ml/g to about 12 ml/g, more preferably from about 8 to about 10.5 ml/g; wherein the tint composition component and the developer composition component are essentially free of surfactant.

BRIEF DESCRIPTION OF THE DRAWINGS

FIG. 1 illustrates an embodiment of the manually-actuable, non-aerosol dispenser cross sectional view;

FIG. 1A is a magnified view, taken along lines 1A-1A of FIG. 1, of a mesh disposed near a diffuser opening or mixing chamber egress orifice of the dispenser;

FIG. 1B is a magnified view, taken along lines 1B-1B of FIG. 1, of a mesh, disposed near a dispenser head orifice;

FIG. 2 is an exploded view of a dispenser head of the dispenser of FIG. 1;

FIG. 3 is a cross-sectional view of an alternate embodiment of the manually-actuable, non-aerosol dispenser of the present disclosure;

FIG. 3A is a magnified view, taken along lines 3A-3A of FIG. 3, of a mesh disposed near a diffuser opening or mixing chamber egress orifice of the dispenser;

FIG. 3B is a magnified view, taken along lines 3B-3B of FIG. 3, of a mesh, disposed near a dispenser head orifice; and FIG. 4 is an exploded view of a dispenser head of the dispenser of FIG. 3.

DETAILED DESCRIPTION OF THE INVENTION

A reduction of surfactants in hair colorant compositions used to produce a foamed product result in most perfumes being insoluble or unstable in the hair colorant compositions due to the hydrophobic nature of perfumes (being essentially oils). Additionally, perfumes having a ClogP higher than desired may cause inhibit or "kill" a foam, leaving a liquid rather than foam in a user's hand. It has been found that careful selection of perfume components via a ClogP criteria results in perfumes that are soluble and stable in the hair colorant composition which is essentially free of surfactants and do not cause foam instability or premature collapse of the foam.

Surfactants are widely used in hair colorant compositions as homogenizing agents and, in the case of foam hair colorants, surfactants are used as foam stabilizing agents. When surfactants are used in foam hair colorants, they may be present in an amount of from 0.1% (1000 ppm) to 20% (200000 ppm) by weight of the composition to be dispensed, typically exemplified in amounts of at least 1.9% (19000 ppm) by weight.

It has been found that when surfactants are present in hair colorant compositions and the compositions are subject to agitation (e.g. vigorous shaking), foam forms in the reservoir of a dispenser having head space. The formation of foam in the reservoir head space leads to dispensing failure.

The hair colorant compositions of the invention do not require the presence of a surfactant to create and maintain foam of acceptable quality. While small amounts of surfactant may be present as process aids, e.g. to assist homogenization of some components, or a function other than foaming, it is preferred that the compositions are substantially free of surfactant.

As used herein "substantially free of surfactant" means that no anionic, cationic, zwitterionic or amphoteric surfactant is purposefully added to the composition. In one embodiment, the composition is substantially free of anionic, cationic, zwitterionic, amphoteric and nonionic surfactants. Surfactants may be present in trace amounts due to presence in components. By "trace amounts" it is intended that the levels of surfactant are less than 500 ppm, such as 0 ppm to 500 ppm. Preferably less than 200 ppm, such as between 0 ppm and 200 ppm. Preferably the levels of surfactants are less than 100 ppm, such as between 0 ppm and 100 ppm. In general the compositions will contain less than 0.05% by weight, preferably less than 0.02% by weight, more preferably less than 0.01% by weight based on the hair colorant composition to be dispensed.

With the reduction or elimination of surfactants from the hair colorant composition, the stability of a perfume in the compositions becomes difficult. As perfumes are essentially oils and hydrophobic in nature, combining perfumes with aqueous based systems essentially free of surfactants pose difficulties. One difficulty identified is the inability to keep perfumes stable within the hair colorant composition components when surfactant is not present or significantly reduced. Another difficulty is that the presence of a perfume can inhibit foam formation or "kills" a foam.

It has been found that a perfume made of a multi-component blend of perfume raw materials in which up to 30% by weight of the perfume consists of essentially perfume raw materials having individual average ClogP in the range 1.5 to 2.5 and the balance of the perfume consists essentially of perfume raw materials having a ClogP of less than 1.5 wherein the entire perfume composition has an Average ClogP of less than 1.5, may be used as a fragrance in the composition of the invention with causing rapid collapse of the foam and which are able to be stably incorporated into the composition. Preferred perfumes comprise a multi-component blend of perfume raw materials each having a ClogP of up to 2.5, wherein the entire perfume composition has an Average ClogP of less than 1.5. It is most preferred that all of the perfume raw materials are stable at a pH of from 9 to 11.

As used herein "Average ClogP" means that the ClogP of the various perfume raw materials with the weight percentage, based upon the weight of the entire perfume composition divided by 100 gives individual average ClogP for each component:

$$\frac{ClogP \times \text{wt \% (by weight of the perfume composition)}}{100}$$

and the sum of the individual average ClogP values gives the Average ClogP.

It has been found that perfume raw materials not meeting the criteria above being present at levels of 500 ppm in the perfume composition cause instability of the perfume composition in the hair colorant composition. Therefore, contaminates (as used herein "contaminates" mean perfume raw materials having a ClogP above 4) should be kept below 500 ppm in the perfume composition.

The logP values of many perfume ingredients are taken from the ratio of the respective concentrations of a compound in the octanol and water partitions of a two-phase system at equilibrium. The concentration measurements are made at a constant temperature of 25° C. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume ingredients which are useful in the present invention. There are existing computational programs that can calculate ClogP values such as the CSLogP-3.0 from ChemiSilico.

The perfume is generally incorporated in the hair colorant compositions in an amount of from 0.05 to 5%, generally 0.1 to 2%, for example 0.3 to 1% by weight of the composition to be dispensed. In the case of a multi-part composition the perfume can be present in one or more of the parts. In the case of a kit for an hair colorant composition the perfume is preferably present in at least the tint formulation component.

TABLE 1

Suitable perfume raw materials having a ClogP less than 1.5 which are stable at pH between 9 and 11 include:

| CAS | Chemical Name |
| --- | --- |
| 110-98-5 | Bis(2-hydroxypropyl)_ether |
| 107-31-3 | METHYLFORMATE |
| 34590-94-8 | DIPROPYLENE_GLYCOL_METHYL_ETHER |
| 1110-65-1 | Ethyl_Maltol |
| 56539-66-3 | 3-Methoxy-3-Methyl_Butanol |
| 71-36-3 | Butyl_alcohol |
| 1569-01-3 | 1-PROPOXY-2-PROPANOL |
| 4798-45-2 | 4-METHYL-1-PENTEN-3-OL |
| 1326-99-5 | Vaniwhite |

TABLE 1-continued

Suitable perfume raw materials having a ClogP less than 1.5 which are stable at pH between 9 and 11 include:

| CAS | Chemical Name |
|---|---|
| 108-95-2 | Hydroxybenzene |
| 57-55-6 | 1,2-PROPANEDIOL |
| 25265-71-8 | Dipropylene_Glycol |
| 22047-25-2 | 2-Acetylpyrazine |
| 111-90-0 | DIETHYLENE_GLYCOL_MONOETHYL_ETHER |
| 8000-41-7 | tert-Butyl_alcohol |
| 123-51-3 | Isopentyl alcohol |
| 15707-23-0 | PYRAZINE,_2-ETHYL-3-METHYL- |
| 100-51-6 | Benzyl alcohol |
| 928-96-1 | cis-3-Hexen-1-ol (aka beta gamma hexenol) |
| 928-95-0 | trans-2-Hexenol |
| 28940-11-6 | Oxalone (aka 7-Methyl-2H-benzo-1,5-dioxepin-3(4H)-one) |
| 60-12-8 | Phenethyl alcohol |
| 1365-19-1 | Linalool oxide |
| 60047-17-8 | Linalool oxide (5) |
| 15707-24-1 | PYRAZINE,_2,3-DIETHYL- |
| 118-71-8 | Maltol |
| 120-57-0 | Heliotropin (aka 3,4-Methylenedioxybenzaldehyde) |
| 122-99-6 | 2-Phenoxyethanol |
| 86803-90-9 | octahydro-5-methoxy-4,7-Methano-1H-indene-2-carboxaldehyde |
| 123-11-5 | p-Anisaldehyde |
| 6413-10-1 | Ethyl 2-methyl-1,3-dioxolane-2-acetate (aka methyl dioxolan) |
| 75-18-3 | DIMETHYLSULFIDE |
| 65416-14-0 | Maltyl isobutyrate |

TABLE 2

Preferred raw materials with a ClogP less than 1.5 include:

| CAS | Chemical Name |
|---|---|
| 7011-83-8 | Methyl_alcohol |
| 57-55-6 | 1,2-PROPANEDIOL |
| 25265-71-8 | Dipropylene_Glycol |
| 110-98-5 | Bis(2-hydroxypropyl)_ether |
| 431-03-8 | Diacetyl |
| 22047-25-2 | 2-Acetylpyrazine |
| 107-31-3 | METHYLFORMATE |
| 3658-77-3 | 4-Hydroxy-2,5-dimethyl-3(2H)-furanone |
| 25395-31-7 | 1,2,3-PROPANETRIOL,_DIACETATE |
| 118-71-8 | Maltol |
| 111-90-0 | DIETHYLENE_GLYCOL_MONOETHYL_ETHER |
| 77-93-0 | Triethyl citrate |
| 97-64-3 | Ethyl_lactate |
| 34590-94-8 | DIPROPYLENE_GLYCOL_METHYL_ETHER |
| 1110-65-1 | Ethyl_Maltol |
| 108-29-2 | gamma-Valerolactone |
| 4940-11-8 | 4H-Pyran-4-one,_2-ethyl-3-hydroxy-(aka ethyl maltol) |
| 5405-41-4 | Butanoic_acid,_3-hydroxy-,_ethyl_ester |
| 8000-41-7 | tert-Butyl_alcohol |
| 141-78-6 | ETHYL_ACETATE |
| 56539-66-3 | 3-Methoxy-3-Methyl_Butanol |
| 141-97-9 | ACETOACETIC_ESTER |
| 71-36-3 | Butyl_alcohol |
| 1569-01-3 | 1-PROPOXY-2-PROPANOL |
| 105-53-3 | DIETHYL_MALONATE |
| 105-37-3 | Ethyl_propionate |
| 695-06-7 | 2(3H)-Furanone,_5-ethyldihydro- |
| 614-18-6 | NICOTINIC_ACID,_ETHYL_ESTER |
| 620-02-0 | 2-FURANCARBOXALDEHYDE,_5-METHYL- |
| 6413-10-1 | Ethyl 2-methyl-1,3-dioxolane-2-acetate |
| 134-96-3 | Syringaldehyde |
| 121-33-5 | Vanillin |
| 4798-45-2 | 4-METHYL-1-PENTEN-3-OL |
| 123-51-3 | Isopentyl alcohol |
| 119-84-6 | 2H-1-Benzopyran-2-one,_3,4-dihydro- |
| 121-34-6 | 4-HYDROXY-3-METHOXYBENZOIC_ACID |
| 120-57-0 | Heliotropin |

TABLE 2-continued

Preferred raw materials with a ClogP less than 1.5 include:

| CAS | Chemical Name |
|---|---|
| 1326-99-5 | Vaniwhite |
| 15707-23-0 | PYRAZINE,_2-ETHYL-3-METHYL- |
| 100-51-6 | Benzyl alcohol |
| 5533-03-9 | VANIWHITE |
| 90-05-1 | 2-METHOXYPHENOL |
| 75-18-3 | DIMETHYLSULFIDE |
| 122-91-8 | Anisyl formate |
| 108-95-2 | Hydroxybenzene |
| 122-99-6 | 2-Phenoxyethanol |
| 120-14-9 | BENZALDEHYDE,_3,4-DIMETHOXY- |
| 110-19-0 | SEC-BUTYLACETATE |
| 928-96-1 | cis-3-Hexen-1-ol |
| 928-95-0 | trans-2-Hexenol |
| 28940-11-6 | Oxalone |
| 65416-14-0 | Maltyl isobutyrate |
| 86803-90-9 | octahydro-5-methoxy-4,7-Methano-1H-indene-2-carboxaldehyde |
| 100-52-7 | Benzaldehyde |
| 123-11-5 | p-Anisaldehyde |
| 122-78-1 | PHENYLACETALDEHYDE |
| 60-12-8 | Phenethyl alcohol |
| 1191-16-8 | Prenyl acetate |
| 104-57-4 | Formic_acid,_phenylmethyl_ester |
| 1365-19-1 | Linalool oxide |
| 60047-17-8 | Linalool oxide (5) |
| 15707-24-1 | PYRAZINE,_2,3-DIETHYL- |

TABLE 3

Suitable, perfume raw materials with a ClogP less than 2.5 include:

| CAS | Chemical Name |
|---|---|
| 7011-83-8 | Methyl_alcohol |
| 57-55-6 | 1,2-PROPANEDIOL |
| 25265-71-8 | Dipropylene_Glycol |
| 110-98-5 | Bis(2-hydroxypropyl)_ether |
| 431-03-8 | Diacetyl |
| 22047-25-2 | 2-Acetylpyrazine |
| 107-31-3 | METHYLFORMATE |
| 3658-77-3 | 4-Hydroxy-2,5-dimethyl-3(2H)-furanone |
| 25395-31-7 | 1,2,3-PROPANETRIOL,_DIACETATE |
| 118-71-8 | Maltol |
| 111-90-0 | DIETHYLENE_GLYCOL_MONOETHYL_ETHER |
| 77-93-0 | Triethyl citrate |
| 97-64-3 | Ethyl_lactate |
| 34590-94-8 | DIPROPYLENE_GLYCOL_METHYL_ETHER |
| 1110-65-1 | Ethyl_Maltol |
| 108-29-2 | gamma-Valerolactone |
| 4940-11-8 | 4H-Pyran-4-one,_2-ethyl-3-hydroxy- |
| 5405-41-4 | Butanoic_acid,_3-hydroxy-,_ethyl_ester |
| 8000-41-7 | tert-Butyl_alcohol |
| 141-78-6 | ETHYL_ACETATE |
| 56539-66-3 | 3-Methoxy-3-Methyl_Butanol |
| 141-97-9 | ACETOACETIC_ESTER |
| 71-36-3 | Butyl_alcohol |
| 1569-01-3 | 1-PROPOXY-2-PROPANOL |
| 105-53-3 | DIETHYL_MALONATE |
| 105-37-3 | Ethyl_propionate |
| 695-06-7 | 2(3H)-Furanone,_5-ethyldihydro- |
| 614-18-6 | NICOTINIC_ACID,_ETHYL_ESTER |
| 620-02-0 | 2-FURANCARBOXALDEHYDE,_5-METHYL- |
| 6413-10-1 | Ethyl 2-methyl-1,3-dioxolane-2-acetate |
| 134-96-3 | Syringaldehyde |
| 121-33-5 | Vanillin |
| 4798-45-2 | 4-METHYL-1-PENTEN-3-OL |
| 123-51-3 | Isopentyl alcohol |
| 119-84-6 | 2H-1-Benzopyran-2-one,_3,4-dihydro- |
| 121-34-6 | 4-HYDROXY-3-METHOXYBENZOIC_ACID |
| 120-57-0 | Heliotropin |
| 1326-99-5 | Vaniwhite |
| 15707-23-0 | PYRAZINE,_2-ETHYL-3-METHYL- |
| 100-51-6 | Benzyl alcohol |

TABLE 3-continued

Suitable, perfume raw materials with a ClogP less than 2.5 include:

| CAS | Chemical Name |
|---|---|
| 5533-03-9 | VANIWHITE |
| 90-05-1 | 2-METHOXYPHENOL |
| 75-18-3 | DIMETHYLSULFIDE |
| 122-91-8 | Anisyl formate |
| 108-95-2 | Hydroxybenzene |
| 122-99-6 | 2-Phenoxyethanol |
| 120-14-9 | BENZALDEHYDE, 3,4-DIMETHOXY- |
| 110-19-0 | SEC-BUTYLACETATE |
| 928-96-1 | cis-3-Hexen-1-ol |
| 928-95-0 | trans-2-Hexenol |
| 28940-11-6 | Oxalone |
| 65416-14-0 | Maltyl isobutyrate |
| 86803-90-9 | octahydro-5-methoxy-4,7-Methano-1H-indene-2-carboxaldehyde |
| 100-52-7 | Benzaldehyde |
| 123-11-5 | p-Anisaldehyde |
| 122-78-1 | PHENYLACETALDEHYDE |
| 60-12-8 | Phenethyl alcohol |
| 1191-16-8 | Prenyl acetate |
| 104-57-4 | Formic acid, phenylmethyl ester |
| 1365-19-1 | Linalool oxide |
| 60047-17-8 | Linalool oxide (5) |
| 15707-24-1 | PYRAZINE, 2,3-DIETHYL- |
| 121-32-4 | Ethyl vanillin |
| 40203-73-4 | Methyl cyclopentylideneacetate |
| 105-54-4 | Ethyl butanoate |
| 63767-86-2 | Guaiacyl acetate |
| 123-86-4 | N-BUTYL ACETATE |
| 91-64-5 | COUMARIN |
| 51519-65-4 | 1,4,4A,7,8,8A-HEXAHYDRO-1,4-METHANONAPHTHALEN-5(6H)-ONE |
| 94087-83-9 | 4-Methoxy-2-Methyl-2-Butanenthiol 1 ppm In DPG |
| 98-86-2 | ACETOPHENONE |
| 6728-26-3 | Trans-2 Hexenal |
| 623-37-0 | 3-HEXANOL |
| 19872-52-7 | 4-Mercapto-4-methylpentanone-2 |
| 134-20-3 | Methyl anthranilate |
| 529-20-4 | 2-METHYLBENZALDEHYDE |
| 3943-74-6 | BENZOIC ACID, 4-HYDROXY-3-METHOXY, METHYL ESTER |
| 104-62-1 | Phenethyl formate |
| 140-11-4 | Benzyl acetate |
| 107-75-5 | Hydroxycitronellal |
| 95-48-7 | o-Cresol |
| 93-35-6 | Umbelliferone |
| 67019-89-0 | 3-Hexanol |
| 106-44-5 | p-Cresol |
| 93-58-3 | BENZOIC ACID, METHYL ESTER |
| 1205-17-0 | 2-Methyl-3-(3,4-methylenedioxyphenyl)-propanal |
| 107-74-4 | Hydroxy-citronellol |
| 87731-18-8 | violiff |
| 4707-47-5 | Veramoss |
| 104-87-0 | P-TOLUALDEHYDE |
| 122-97-4 | Hydrocinnamyl alcohol |
| 100-47-0 | BENZONITRILE |
| 67845-46-9 | p-Methyl phenoxy acetaldehyde |
| 104-54-1 | CINNAMYL ALCOHOL |
| 1504-74-1 | o-Methoxycinnamaldehyde |
| 5471-51-2 | para-hydroxy phenyl butanone |
| 100-06-1 | Para Methoxy Acetophenone |
| 67801-65-4 | 3,6-Dimethyl-3-cyclohexene-1-carboxaldehyde |
| 104-21-2 | Benzenemethanol, 4-methoxy-, acetate |
| 94201-19-1 | Methyl Laitone 10% TEC |
| 40527-42-2 | Heliotropine diethyl acetal |
| 4430-31-3 | Octahydrocoumarin |
| 93-51-6 | 4-Methyl-2-methoxyphenol |
| 150-78-7 | P-DIMETHOXYBENZENE |
| 1123-85-9 | Hydratopic alcohol |
| 101-41-7 | Methyl phenylacetate |
| 97-54-1 | Isoeugenol |
| 111-27-3 | Caproyl alcohol |
| 123-92-2 | Isoamyl acetate |
| 55418-52-5 | Piperonyl acetone |
| 66327-54-6 | Methyl 3-(2-furyl)acrylate |
| 64988-06-3 | beta-Phenoxy ethyl acetate |
| 24683-00-9 | 2-Isobutyl-3-methoxypyrazine |
| 66-25-1 | HEXANAL |
| 104-55-2 | Cinnamic aldehyde |
| 93-53-8 | Benzeneacetaldehyde, .alpha.-methyl- |
| 67633-96-9 | Liffarome |
| 85-91-6 | Benzoic acid, 2-(methylamino)-, methyl ester |
| 108-64-5 | Ethyl isovalerate |
| 67634-16-6 | 2,4-Dimethyl-3-cyclohexene-1-methanol |
| 67633-94-7 | 2-Methylbutyl acetate |
| 63500-71-0 | Florol (aka 2-isobutyl-4-hydroxy-4-methyltetrahydropyran) |
| 484-20-8 | Bergapten(e) |
| 20665-85-4 | Vanillin isobutyrate |
| 68039-44-1 | 5-Methylhexanoic acid |
| 2102-58-1 | 1-Carveol |
| 65-85-0 | BENZOIC ACID |
| 538-86-3 | BENZYL METHYL ETHER |
| 501-52-0 | BETA-PHENYLPROPIONIC ACID |
| 7452-79-1 | Ethyl 2-methylbutyrate |
| 7493-74-5 | Allyl phenoxyacetate |
| 138-87-4 | beta-Terpineol |
| 23911-56-0 | Nerolione |
| 471-16-9 | Bicyclo 3.1.0 hexan-3-ol, 4-methylene-1-(1-methy |
| 18096-62-3 | 4,4a,5,9b-tetrahydroindeno[1,2-d]-1,3-dioxin |
| 92015-65-1 | KOUMALACTONE 953320 |
| 104-50-7 | gamma-Octalactone |
| 31906-04-4 | Lyral |
| 110-93-0 | 5-Hepten-2-one, 6-methyl- |
| 3391-86-4 | 1-Octenol-3 |
| 2568-25-4 | Benzaldehyde propylene glycol acetal |
| 586-81-2 | Gamma Terpineol |
| 539-82-2 | ETHYL VALERATE |
| 119-36-8 | METHYL SALICYLATE |
| 3681-71-8 | cis-3-Hexenylacetate |
| 93-28-7 | Eugenyl acetate |
| 97-53-0 | Eugenol |
| 628-63-7 | n-Pentyl acetate |
| 103-45-7 | B-PHENYLETHYL ACETATE |
| 101-48-4 | Phenylacetaldehyde dimethyl acetal |
| 18640-74-9 | 2-Isobutylthiazole |
| 21368-68-3 | CAMPHOR GUM |
| 464-49-3 | CAMPHOR GUM |
| 65405-72-3 | m-Tolyl aldehyde |
| 72402-00-7 | Plinol |
| 24168-70-5 | 2-Methoxy-3-(1-methylpropyl)pyrazine |
| 101-39-3 | alpha-Methylcinnamic aldehyde |
| 2550-26-7 | 2-Butanone, 4-phenyl- |
| 122-00-9 | 4-Methylacetophenone |
| 98-55-5 | alpha-Terpineol |
| 1301-15-2 | Canthoxal |
| 562-74-3 | 4-Terpinenol |
| 22457-23-4 | Stemone |
| 121-39-1 | Ethyl 3-phenylglycidate |
| 536-60-7 | Benzenemethanol, 4-(1-methylethyl)- |
| 120-72-9 | INDOLE |
| 93-92-5 | Methyl Phenyl Carbinyl Acetate |
| 100-86-7 | Dimethyl benzyl carbinol |
| 105-67-9 | 2,4-Xylenol |
| 103-26-4 | CINNAMIC ACID, METHYL ESTER |
| 89-79-2 | Isopulegol |
| 2497-18-9 | 2-Hexen-1-yl acetate |
| 122-63-4 | Benzyl propionate |
| 93-89-0 | Ethyl benzoate |
| 104-09-6 | Syringa Aldehyde |
| 142653-61-0 | PARMANYL 3/055119 |
| 586-82-3 | p-Menth-3-en-1-ol |
| 1197-01-9 | p,alpha,alpha-Trimethylbenzyl alcohol |
| 16251-77-7 | 3-Phenylbutanal |
| 103-54-8 | Cinnamyl acetate |
| 68039-49-6 | 2,4-Dimethyl-3-Cyclohexene-1-carboxaldehyde |
| 68039-49-6 | 2,4-Dimethyl-3-Cyclohexene-1-carboxaldehyde |
| 20125-84-2 | cis-3-Octen-1-ol |
| 1632-73-1 | Fenchyl alcohol |
| 4442-79-9 | CYCLOHEXANEETHANOL |
| 124-76-5 | Isoborneol |
| 464-45-9 | 1-Borneol |
| 189440-77-5 | Anapear |

TABLE 3-continued

Suitable, perfume raw materials with a ClogP less than 2.5 include:

| CAS | Chemical Name |
|---|---|
| 5986-38-9 | Ocimenol |
| 116-02-9 | 3,3,5-Trimethylcyclohexanol |
| 141-92-4 | Hydroxycitronellal dimethyl acetal |
| 4360-47-8 | CINNAMALVA |
| 1438-91-1 | Furfuryl methyl sulfide |
| 105-68-0 | 1-Butanol, 3-methyl-, propanoate |
| 68527-77-5 | 1,2,4-(or 1,3,5)-Trimethyl-3-cyclohexene-1-methanol |
| 5392-40-5 | Citral |
| 84-66-2 | DIETHYL PHTHALATE |
| 1195-79-5 | FENCHONE |
| 78-70-6 | Linalool |
| 1885-38-7 | 3-PHENYL-2-PROPENENITRILE |
| 30772-79-3 | 4,7-Methano-1H-indenecarboxaldehyde, octahydro-, exo-, exo-, |
| 58461-27-1 | Lavandulol |
| 5462-06-6 | Anisylpropanal |
| 507-70-0 | Borneol |
| 101-97-3 | BENZENEACETIC ACID, ETHYL ESTER |
| 99-49-0 | CARVONE |
| 3558-60-9 | Methyl phenethyl ether |
| 2563-07-7 | Ultravanil 51435Tt |
| 110-43-0 | Methyl pentyl ketone |
| 67634-00-8 | Allyl amyl glycolate |
| 111-71-7 | HEPTANAL |
| 91-62-3 | 6-Methylquinoline |
| 239-88-1 | Efetaal |
| 66576-71-4 | Isopropyl 2-methylbutyrate |
| 64001-15-6 | Octahydro-4,7-methanoindan-5(6)-yl acetate |
| 7786-44-9 | 2,6-Nonadien-1-ol |
| 5948-04-9 | d-Dihydrocarvone |
| 7764-50-3 | Dihydrocarvone |
| 620-17-7 | M-ETHYLPHENOL |
| 28069-72-9 | (2E,6Z)-Nona-2,6-dien-1-ol |
| 4180-23-8 | trans-Anethole |
| 27135-90-6 | Verdalia A |
| 13254-34-7 | 2-Heptanol, 2,6-dimethyl- |
| 933-48-2 | Cyclohexanol, 3,3,5-trimethyl-, cis- |
| 104-61-0 | gamma-Nonalactone |
| 106-24-1 | GERANIOL |
| 106-25-2 | Nerol |
| 32764-98-0 | 6-(Z,3-Pentenyl)-tetrahydro-(2H)-pyranone-2 |
| 90-87-9 | Hydratropaldehyde dimethyl acetal |
| 6485-40-1 | L-Carvone |
| 94-59-7 | SAFROLE |
| 68901-15-5 | Cyclogalbanate |
| 18479-58-8 | Dihydromyrcenol |
| 2785-89-9 | Phenol, 4-ethyl-2-methoxy- |
| 72903-27-6 | Fructalate |
| 53018-24-9 | VERDALIA A |
| 75147-23-8 | 1,5-Dimethyl-bicyclo[3.2.1]octan-8-one, oxime- |
| 103694-68-4 | Majantol |

Other ingredients, whether conventionally used in hair colorant compositions or not may be included if desired and not adverse to the formation of foam in the essential absence of surfactant (which may only be present in trace quantities as indicate above). Hence evaluation of any additional ingredient versus the overall composition functionality is needed and exclusion of components resulting in premature foam collapse, such as oily or greasy substances, is advisable.

It has been found that certain materials, which are not surfactants, are capable of acting as foam stabilizing agents in hair colorant compositions. As used herein "foam stabilizing agents" include not only components that can help to stabilize the liquid film of the foam bubbles, but components that may also generate foam. Therefore foaming agents are included in the meaning of foam stabilizing agents. These desired agents allow stable foams of the hair colorant composition to be formed and maintained for the desired timeframe.

Foam Formation and Stability

Foam consists of a dispersion of gas bubbles in a liquid. Bubbles of gas rupture on contact with each other and additives are needed to retard this contact. The bilayer films between two bubbles in foam are fairly flat surfaces while the surfaces at plateau borders where three bubbles meet are curved. There are known chemical-physical properties which slow down or even stop the film thinning process caused by drainage and stabilize the foam.

Foam Stabilizing Agents

The foam stabilizing agents used in the compositions of the invention are selected to provide foaming benefits and/or foam stabilization benefits and are stable in the presence of an oxidizing agent such as hydrogen peroxide or peroxymonocarbonate ions or in the presence of alkaline pHs (such as that found in tint compositions). Suitable foam stabilizing agents include polymeric foam stabilizers and polymeric emulsifiers. The foaming stabilizing agents of the present composition are essentially free of surfactants traditionally used for foam formation and stabilization. Combinations of polymeric emulsifiers and polymeric foam stabilizers are also embodied herein.

Polymeric Foam Stabilizers

Polymeric foam stabilizing agents suitable for use herein include cellulose materials such as methylcellulose (hydroxypropyl methylcellulose sold as METHOCEL 40-101 and methylcellulose sold as METHOCEL A4MP) and ethylcellulose (Cecetyl hydroxyethylcellulose sold as NATROSOL PLUS).

The hydroxypropyl methylcellulose may have the general structure of:

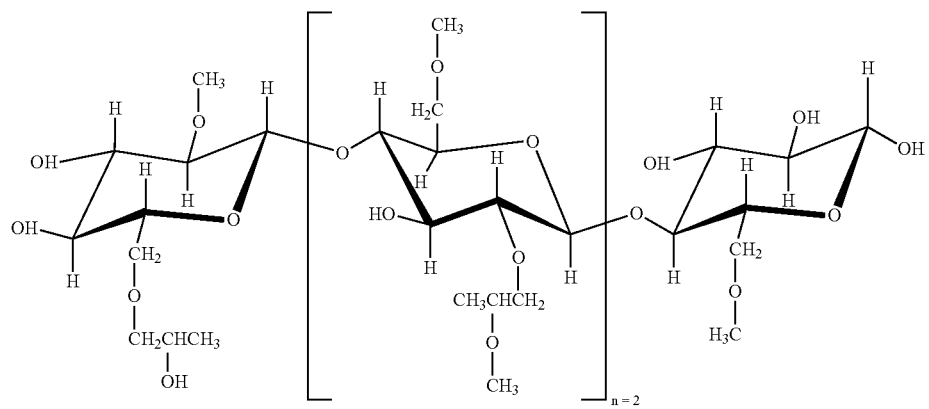

The methylcellulose may have the general structure of:

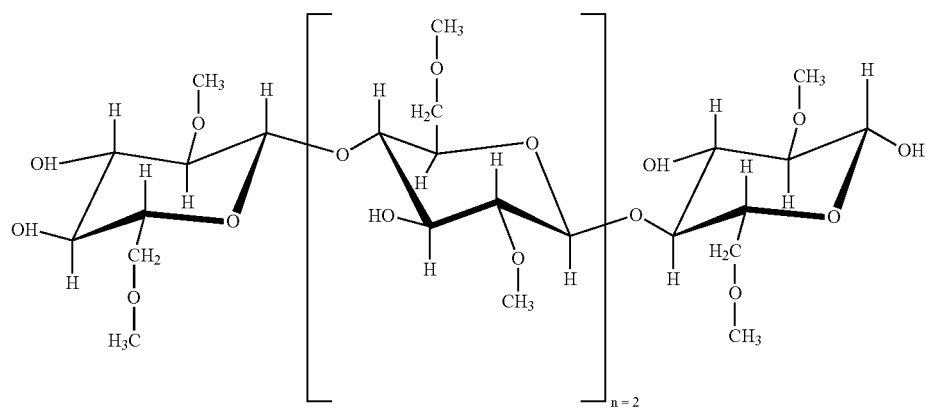

The "n" of these structures is selected to give the desired viscosity. The METHOCEL 40-101 has a viscosity of about 75,000 mPa s (for a 2% aqueous solution at 20° C. with a Ubbelohde tube viscometer) and the METHOCEL A4MP has a viscosity of about 4000-5000 mPa s (for a 2% aqueous solution at 20° C. with a Ubbelohde tube viscometer).

Another suitable foam stabilizing agent includes (meth) acrylic polymers such as Acrylates/$C_{10-30}$ alkyl acrylate crosspolymer, a copolymer of $C_{10-30}$ alkyl acrylates and one or more monomers of acrylic acid, methacrylic acid or one of their simple esters crosslinked with an allyl ether of sucrose or an allyl ether of pentaerythritol. It is commercially available from Goodrich as PEMULEN TR-1 and PEMULEN TR-2. PEMULEN TR-1 polymer is preferred. CAPIGEL 98, an acrylates copolymer produced by SEPPIC.

Another suitable foam stabilizing agent suitable for use herein is a hydrophobically-modified alkali soluble emulsion polymer synthesized through an emulsion polymerization process from an acid/acrylate copolymer backbone and a monomer that connects the hydrophobic groups as side chains. An example of such a material is ACULYN™ 22, commercially available from Rohm Haas, which is synthesized from acrylic acid, acrylate esters and a steareth-20 methacrylate ester with an INCI name of Acrylates/Steareth-20 Methacrylate Copolymer.

Another suitable foam stabilizing agent includes anionic alkali-soluble polymer emulsion synthesized from acid and acrylate co-monomers through emulsion polymerization. An example of such a material is ACULYN™ 33, commercially available from Rohm Haas with an INCI name of Acrylates Copolymer.

Mixtures of ACULYN™ 22 and ACULYN™ 33 may be used. One embodiment utilizes a mixture of ACULYN™ 22 and ACULYN™ 33 in a ratio (weight) of 5:1 to 1:5 weight ratio based upon the weight of the composition or based upon the weight of the developer composition. In one embodiment, a mixture of ACULYN™ 22 and ACULYN™ 33 in a ratio (weight) of 1:3 to 1:4 by weight of the developer composition is utilized. In one embodiment, a mixture of ACULYN™ 22 and ACULYN™ 33 in a ratio (weight) of 4:1 to 1:1 by weight of the developer composition (containing the oxidising agent) is utilized.

Polyquaternium-55, a polymer comprising vinyl pyrrolidone (VP), dimethylaminopropyl methacrylamide (DMAPA) and methacryoylaminopropyl lauryldimonium chloride (MAPLAC) is also suitable for use herein and has the following generalized structure:

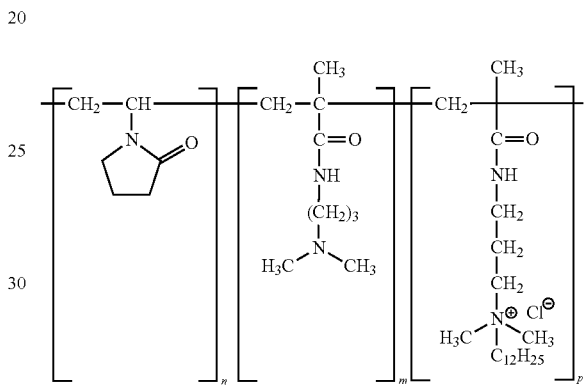

Polyquaternium-55 is sold under the tradename STYLEZE® in a 10 and 20 variation. The n, m and p levels depend on the monomer ratio. The STYLEZE®-10 has a monomer ratio of 0.85VP:0.11DMAPA:0.4MAPLAC. The STYLEZE®-20 has a monomer ratio of 0.85VP: 0.11DMAPA:0.4MAPLAC.

Another suitable foam stabilizing agent includes a polyoxyethylene, polyoxypropylene block polymer that conforms generally to the formula shown below in which the average values of x, y and z are respectively 31, 54 and 31.

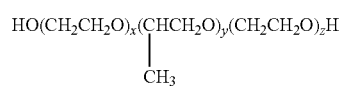

sold under the tradename POLOXAMER 334.

Another suitable foam stabilizing agent includes a polyethyleneoxide-polypropyleneoxide-polyethyleneoxide block polymer terminating in primary hydroxyl groups sold under the tradename PLURONIC P104 and PLURONIC F108 (ex. BASF).

Polymeric Emulsifiers

Suitable polymeric materials for use as a foam emulsifing agent include polysaccharides, cellulosic materials, amine-bearing polymers, acidic polymers obtainable from natural sources, chemically modified starches, carboxyvinyl polymers, polyvinylpyrrolidone, polyvinyl alcohol, polyacrylic acid polymers, polymethacrylic acid polymers, polysiloxanes and mixtures thereof.

Suitable polysaccharides include xanthan gum, carrageenin gum, guar-guar, cationic guars, hydroxypropyl guar gum, agar-agar, locust bean gum, alginates, tyloses, salts of any of these materials (such as sodium salts) and mixtures thereof.

Suitable cellulosic materials include cellulose ethers, such as carboxymethylcellulose, ethylcellulose, hydroxypropylcellulose, methylcellulose, cellulose mixed ethers, such as carboxymethylhydroxyethylcellulose, ethylhydroxyethylcellulose, methoxyhydroxyalkylcelluloses, methylhydroxyalkylcelluloses, such as methylhydroxyethylcellulose, methylhydroxypropylcellulose, methylhydroxybutylcellulose; and mixtures of these.

Suitable amine-bearing polymers include deacytylated chitin, sometimes known as chitosan, which as been modified to be soluble in basic conditions usually by alkylation or by carboxymethylation, but other modifications of chitin are also suitable. See *Chitosan Derivatives Obtained By Chemical Modifications For Biomedical And Environmental Applications*; International Journal of Biological Macromolecules; Volume 43, Issue 5, 1, Dec. 2008, Pages 401-414.

Suitable polysiloxanes include dimethylpolysiloxanes, methylphenylpolysiloxanes, cyclic silicones as well as silicone compounds modified by amino, fatty acid, alcohol, polyether, epoxy, fluoro, glycoside and or alkyl groups. Preferred as silicone compounds according to the present invention are polysiloxane-polyether copolymers aka dimethicone copolyol, which are available from the company named Goldschmidt AG of Essen under the trade name ABIL®, especially polysiloxane-polyether copolymers of the B 88 product family, such as ABIL® B 8843, ABIL® B 8851, ABIL® B 8852, ABIL® B 8863, ABIL® B 88183 and ABIL® B 88184.

The foaming stabilizing agent is present in the oxidizing hair colorant composition to be dispensed in an amount sufficient to allow formation and/or stabilization of foam without need for a surfactant. Thus, there is sufficient foam stabilizing agent present to form and/or maintain foam when the composition is substantially free of surfactant. Generally, the foam stabilizing agent will be present in an amount of from 1 to 25% by weight, preferably 2 to 15% by weight, more preferably 2 to 10% by weight of the hair colorant composition. In the case of a multi-part kit, the foam stabilizing agent may be present in one or more of the components. Preferably, the foam stabilizing agent is present in the component containing the oxidizing agent (developer) since a single developer composition may be used with a plurality of different hair dye (tint) formulations that form several different hair shade colors. The foam stabilizing agent may be present in the developer composition from 1 to 25% by weight, preferably 2 to 20% by weight, preferably from 5% to 20% by weight of the developer composition.

Foam

As used herein "foam" means a personal care composition which after being passed through a manually-actuable, non-aerosol dispenser has bubbles that sustain their shape and give a volume independent of any type of container. It is preferably that the volume is a foam specific volume from about 6 mL/g to about 14 mL/g, such as about 7.5 mL/g to about 12 mL/g, such as from about 8 mL/g to about 11 mL/g. One embodiment is a foam specific volume of about 10 mL/g.

As used herein "stroke" means deflecting a reservoir that is placed against a vertical flat surface, such as a wall, on the side of the reservoir opposite the wall, 30 mm towards the wall at a rate of 20 mm per second. "Squeeze" or "dispensed" are also included in the term "stroke".

A manually-actuable, non-aerosol dispenser is optionally designed to have a foam output per stroke or squeeze from about 0.5 gram/stroke to about 5.0 gram/stroke, preferably about 0.8 gram/stroke to about 4.0 gram/stroke, preferably from about 1.0 gram/stroke to about 4.0 gram/stroke. In one embodiment, the manually-actuable, non-aerosol dispenser is optionally designed to have a foam output per stroke or squeeze from about 1.8 gram/stroke to about 2.2 gram/stroke.

A manually-actuable, non-aerosol dispenser is optionally designed to have a foam output per stroke or squeeze from about 3 mL/stroke to about 70 mL/stoke, preferably from about 76 mL/stroke to about 48 mL/stroke, preferably from about 8 mL/stroke to about 44 mL/stroke, preferably from about 18 mL/stroke to about 22 mL/stroke.

The minimum time for the foam to retain its volume is at least long enough to transfer from a user's hand to the desired location, such as on the hair, e.g. the foam substantially maintains its shape and foam specific volume. A preferred minimum time is for at least 10 seconds, for example at least 12, or at least 15 seconds. It could be longer minimum time if a quantity of foam, e.g. a bowl full by a hair dresser, is generated and spreading on the head only starts once the bowl full is readily made, such as 5 minutes or such as 10 minutes.

In order to fulfill the coloring action, hair colorant compositions need to reach and disperse on the hair. Hence a foam hair color composition needs to collapse within the time usually allocated for hair coloring (e.g., 10 to 30 minutes). The collapse of the foam could be as quickly as 3 to 10 minutes but may be up to 15 minutes, or up to 30 minutes. The amount of sebum on hair can affect the foam and cause it to collapse. The more sebum on the hair, the faster the foam collapses on the hair.

Rheology Profile

The hair colorant composition has a desired rheological profile during usage that ensures a desired user experience when in contact with the hair colorant composition. The composition of the present invention is subject to different stress/strain forces during the consumer's use of the formulation. The formulation is subject to mixing of two components together to form the desired hair colorant composition, such as shaking of a container holding the two components. The formulation is then foamed by passing it through the foaming means, such as a squeeze foaming engine and is dispensed into a user's hand. The formulation is then applied to the desired surface, such as hair, and the foam collapses and forms a liquid on the desired surface, such as hair. The desired resulting viscosity of the hair colorant composition after the collapse of the foamed hair colorant composition is selected such that the composition does not drip or run from the surface on which it is applied, such as hair on the head of a user.

As used herein "low shear viscosity" means a composition is measured at a shear rate $0.01$ $s^{-1}$ according to the method below. The low shear viscosity is believed to represent (1) the viscosity of the composition as it sits in the reservoir and (2) the viscosity of the composition "post-foam collapse". In other words, the post-foam collapse is when the composition is foamed by the dispenser and then the foam collapses. The low shear viscosity in the rheology profile contributes to reducing the amount of foam generated in the head space in the reservoir when the composition is mixed or shaken by a user. Further, the low shear viscosity in the rheology profile of the composition post-foam collapse is important with respect to whether the composition stays on the desired surface or if the composition runs or drips from the surface after the foam collapses. The low shear viscosity of the hair coloring composition is above 1000 mPa s (1000 cps), preferably from about 1000 mPa s (1000 cps) to about 10,000 mPa s (10,000 cps), preferably from about 2000 mPa s (2000 cps) to about 9000 mPa s (9000 cps), and preferably from about 2000 mPa s (2000 cps) to about 5000 mPa s (5000 cps).

As used herein "high shear viscosity" means a composition is measured at a shear rate 500 s$^{-1}$ according to the method below. The high shear viscosity is believed to represent the viscosity of the hair colorant composition moving from the reservoir to the dispensing head orifice, usually through a foaming means such as the mixing chamber. The high shear viscosity of the hair colorant composition is less than 200 mPa s (200 cps), preferably less than 100 mPa s (100 cps), preferably from about 1 mPa s (1 cps) to about 200 mPa s (200 cps).

Additional Hair Colorant Ingredients

Solvent

The hair colorant composition may comprise solvents such as water, lower aliphatic alcohols, for example aliphatic alcohols with from 1 to 4 carbon atoms such as ethanol, propanol and isopropanol, or glycols such as glycerin and 1,2-propylene glycol. The solvents may be utilized for the hair colorant composition or in pre-composition components such as the tint composition or developer composition in concentrations of from 0.1 to 30% by weight.

Alkalizing Agent

The hair colorant composition, generally in a tint composition, comprises an alkalizing agent, preferably a source of ammonium ions or ammonia. Any alkalizing agent known in the art may be used such as alkanolamides for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, guanidium salts, and alkali metal and ammonium hydroxides and carbonates, such as sodium hydroxide and ammonium carbonate. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia and mixtures thereof. Suitable alkalizing agents also include acidulents, such as inorganic and organic acids, e.g., phosphoric acid, acetic acid, ascorbic acid, citric acid or tartaric acid, hydrochloric acid, and mixtures thereof.

The hair colorant composition or the tint composition may comprise from about 0.1% to about 10% by weight, such as from about 0.5% to about 5%, such as from about 1% to about 3% of an alkalizing agent, such as a source of ammonium ions.

Oxidizing Agent

The hair colorant compositions herein, generally in the developer composition, may comprise at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilization and decolorization of the melanin (bleaching) and accelerate the oxidation of the oxidative dye precursors (oxidative dyeing) in the hair shaft.

The oxidizing agent may be selected from water-soluble oxidizing agents which are inorganic peroxygen materials capable of yielding hydrogen peroxide in an aqueous solution. The oxidizing agents may be provided in aqueous solution or as a powder which is dissolved prior to use. Water-soluble oxidizing agents include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can also be used if desired. Preferred for use in the compositions according to the present invention are hydrogen peroxide, percarbonate, persulphates and combinations thereof.

The oxidative agent may comprise from about 0.1% to about 40% by weight, preferably from about 1% to about 30% by weight, and most preferably from about 2% to about 30% by weight of the hair colorant composition or developer composition. Another potential oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH (of the hair care composition) of up to and including 9.5, preferably 7.5 to 9.5 more preferably about pH 9. Moreover, this system is also particularly effective in combination with a source of ammonia or ammonium ions. It has been found that this oxidizing agent can deliver improvements to the desired hair color results particularly with regard to the delivery of high lift, whilst considerably reducing the odor, skin and scalp irritation and damage to the hair fibers.

Accordingly, any source of these peroxymonocarbonate ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and as an oxidizing agent. Preferred sources of carbonate ions, carbamate and hydrocarbonate ions are sodium hydrogen carbonate, potassium hydrogen carbonate, ammonium carbamate, and mixtures thereof.

The oxidative agent may comprise from about 0.1% to about 15% by weight, preferably from about 1% to about 10% by weight, and most preferably from about 1% to about 8% by weight of a hydrogencarbonate ion and from about 0.1% to about 10% by weight, preferably from about 1% to about 7% by weight, and most preferably from about 2% to about 5% by weight of the oxidative agent of a source of hydrogen peroxide.

pH

The hair colorant compositions of the present invention may have a pH of from 8 to 12, preferably from 8 to 10. For embodiments comprising a peroxymoncarbonate ion, the pH is preferably up to and including pH 9.5, more preferably from about 9.5 to about 7.5, even more preferably from about 9.5 to about 8.4, most preferably from about 9.4 to about 8.5, and even more preferably about pH 9.3 or 9.0.

Any sub-components of the hair colorant compositions, such as a tint composition or a developer composition may have a different pH from the hair colorant composition. For example, if the tint composition comprises an alkalizing agent, the tint composition will have an alkaline pH, such as higher than 8.

The pH of the compositions can be determined by using either a Mettler Toledo MP220 or a MP225 pH equipment, fitted with a standard laboratory pH electrode. The equipment is calibrated before each use using standard calibration buffers and using the standard calibration procedure.

Hair Dye

The hair colorant composition contains a hair dye which may be selected from those known in the art, e.g. oxidative dye precursors, through which the coloring is produced by the action of oxidizing agents, such as for example hydrogen peroxide, or in the presence of atmospheric oxygen (if necessary with the addition of a suitable enzyme system). The hair dye may be a oxidative dye precursor, a direct dye or a mixture thereof.

Oxidative Dye Precursors

The hair care compositions or a sub-component thereof (tint composition) may include oxidative dye precursor in the form of primary intermediates or couplers. The compounds suitable for use in the hair colorant compositions (including those optionally added), in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic hydroxyl groups, in the form of their salts with bases, such as alkali phenolates.

These compounds are well known in the art, and include aromatic diamines, aminophenols, aromatic diols and their derivatives (a representative but not exhaustive list of oxidation dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein. These are: 1,7-Dihydroxynaphthalene (1,7-NAPHTHALENEDIOL); 1,3-Diaminobenzene (m-PHENYLENEDIAMINE); 1-Methyl-2,5-diaminobenzene (TOLUENE-2,5-DIAMINE); 1,4-Diaminobenzene (p-PHENYLENEDIAMINE); 1,3-Dihydroxybenzene (RESORCINOL); 1,3-Dihydroxy-4-chlorobenzene, (4-CHLORORESORCINOL); 1-Hydroxy-2-aminobenzene, (o-AMINOPHENOL); 1-Hydroxy-3-aminobenzene (m-AMINOPHENOL); 1-Hydroxy-4-amino-benzene (p-AMINOPHENOL); 1-Hydroxynaphthalene (1-NAPHTHOL); 1,5-Dihydroxynaphthalene (1,5-NAPHTHALENEDIOL); 2,7-dihydroxynaphthalene (2,7-NAPHTHELENEDIOL); 1,4-Dihydroxybenzene (HYDROQUINONE); 1-Hydroxy-4-methylaminobenzene (p-METHYLAMINOPHENOL); 6-Hydroxybenzo-morpholine (HYDROXYBENZOMORPHOLINE); 1-Methyl-2-hydroxy-4-aminobenzene (4-AMINO-2-HYDROXY-TOLUENE); 1-Methyl-2-hydroxy-4-(2'-hydroxyethyl)aminobenzene (2-METHYL-5-HYDROXY-ETHYLAMINO-PHENOL); 1,2,4-Trihydroxybenzene (1,2,4-TRIHYDROXYBENZENE); 1-Phenol-3-methylpyrazol-5-on (PHENYLMETHYLPYRAZOLONE); 1-(2'-Hydroxyethyloxy)-2,4-diaminobenzene (2,4-DIAMINOPHENOXY-ETHANOL HCL); 1-Hydroxy-3-amino2,4-dichlorobenzene (3-AMINO-2,4-DICHLORO-PHENOL); 1,3-Dihydroxy-2-methylbenzene (2-METHYLRESORCINOL); 1-Amino-4-bis-(2'-hydroxyethyl)aminobenzene (N,N-BIS(2-HYDROXY-ETHYL)-p-PHENYLENE-DIAMINE); 2,4,5,6-Tetraminopyrimidine (HC Red 16); 1-Hydroxy-3-methyl-4-aminobenzene (4-AMINO-m-CRESOL); 1-Hydroxy-2-amino-5-methylbenzene (6-AMINO-m-CRESOL); 1,3-Bis-(2,4-Diaminophenoxy)propane (1,3-BIS-(2,4-DIAMINO-PHENOXY)-PROPANE); 1-(2'-Hydroxyethyl)-2,5-diaminobenzene (HYDROXYETHYL-p-PHENYLENE DIAMINE SULPHATE); 1-Methoxy-2-amino-4-(2'-hydroxyethylamino)benzene, (2-AMINO-4-HYDROXY-ETHYLAMINOANISOLE); 1-Hydroxy-2-methyl-5-amino-6-chlorobenzene (5-AMINO-6-CHLORO-o-CRESOL); 1-Hydroxy-2-amino-6-methylbenzene (6-AMINO-o-CRESOL); 1-(2'-Hydroxyethyl)-amino-3,4-methylenedioxybenzene (HYDROXYETHYL-3,4-METHYLENE-DIOXY-ANILINE HCl); 2,6-Dihydroxy-3,4-dimethylpyridine (2,6-DIHYDROXY-3,4-DIMETHYLPYRIDINE); 3,5-Diamino-2,6-dimethoxypyridine (2,6-DIMETHOXY-3,5-PYRIDINEDIAMINE); 5,6-Dihydroxyindole (5,6-DIHYDROXY-INDOLE); 4-Amino-2-aminomethylphenol (2-AMINOETHYL-p-AMINO-PHENOL HCl); 2,4-Diamino-5-methylphenetol (2,4-DIAMINO-5-METHYL-PHENETOLE HCl); 2,4-Diamino-5-(2'-hydroxyethyloxy) toluene (2,4-DIAMINO-5-METHYL-PHENOXYETHANOL HCl); 5-Amino-4-chloro-2-methylphenol (5-AMINO-4-CHLORO-o-CRESOL); 1,3-Bis(N(2-Hydroxyethyl)N(4-amino-phenyl)amino)-2-propanol (HYDROXYPROPYL-BIS-(N-HYDROXY-ETHYL-p-PHENYLENEDIAMINE)HCL); 6-Hydrorxyindole (6-HYDROXY-INDOLE); 2,3-Indolinedione (ISATIN); 3-Amino-2-methylamino-6-methoxy-pyridine (HC BLUE NO. 7); 1-Phenyl-3-methyl-5-pyrazolone (2,4-DIHYDRO-5-METHYL-2-PHENYL-3H-PYRAZOL-3-ONE); 2-Amino-3-hydroxypyridine (2-AMINO-3-HYDROXYPYRIDINE); 5-Amino-salicylic acid; 1-Methyl-2,6-bis(2-hydroxy-ethylamino)benzene (2,6-HYDROXYETHYLAMINO-TOLUENE); 4-Hydroxy-2,5, 6-triaminopyrimidine (2,5,6-TRIAMINO-4-PYRIMIDINOL SULPHATE); 2,2'-[1,2-Ethanediyl-bis-(oxy-2,1-ethanediyloxy)]-bis-benzene-1,4-diamine (PEG-3,2',2'-DI-p-PHENYLENEDIAMINE); 5,6-Dihydroxyindoline (DIHYDROXYINDOLINE); N,N-Dimethyl-3-ureidoaniline (m-DIMETHYL-AMINO-PHENYLUREA); 2,4-Diamino-5-fluortoluenesulfatehydrate (4-FLUORO-6-METHYL-m-PHENYLENEDIAMINE SULPHATE); 1-Acetoxy-2-methylnaphthalene (1-HYDROXYYETHYL-4,5-DIAMINOPYRAZOLE SULPHATE); 1-acetoxy-2-methylnaphthalene (2-METHYL-1-NAPHTHOL); 2-amino-5-ethylphenol (2-AMINO-5-ETHYLPHENOL); 2,4-dichloro-3-aminophenol (3-AMINO-2,4-DICHLOROPHENOL); and p-Anilinoaniline (N-PHENYL-P-PHENYLENEDIAMINE).

Direct Dyes

The hair colorant compositions may also comprise compatible direct dyes, in an amount sufficient to provide coloring, particularly with regard to intensity. Typically, such an amount will range from about 0.05% to about 4%, by weight of the hair colorant composition of a sub-component such as a tint composition. Suitable direct dyes include but are not limited to: Acid Yellow 1; Acid Orange 3; Disperse Red 17; Basic Brown 17; Acid Black 52; Acid Black 1; Disperse Violet 4; 4-nitro-o-phenylenediamine; 2-nitro-p-phenylenediamine; Picramic Acid; HC Red No. 13; 1,4-bis-(2'-hydroxyethyl)-amino-2-nitrobenzene; HC Yellow No. 5; HC Red No. 7; HC Blue No. 2; HC Yellow No. 4; HC Yellow No. 2; HC Orange No. 1; HC Red No. 1; 2-chloro-5-nitro-N-hydroxyethyl-p-phenylenediamine; HC Red No. 3; 4-amino-3-nitrophenol; 2-hydroxyethylamino-5-nitroanisole; 3-nitro-p-hydroxyethylaminophenol; 2-amino-3-nitrophenol; 6-nitro-o-toluidine; 3-methylamino-4-nitrophenoxyethanol; 2-nitro-5-glycerylmethylaniline; HC Yellow No. 11; HC Violet No. 1; HC Orange No. 2; HC Orange No. 3; HC Yellow No. 9; 4-nitrophenyl aminoethylurea; HC Red No. 10; HC Red No. 11; 2-hydroxyethyl picramic acid; HC Blue No. 12; HC Yellow No. 6; hydroxyethyl-2-nitro-p-toluidine; HC Yellow No. 12; HC Blue No. 10; HC Yellow No. 7; HC Yellow No. 10; HC Blue No. 9; N-ethyl-3-nitro PABA; 4-amino-2-nitrophenyl-amine-2'-carboxylic acid; 2-chloro-6-ethylamino-4-nitrophenol; 6-nitro-2,5-pyridinediamine; HC Violet No. 2;

2-amino-6-chloro-4-nitrophenol; 4-hydroxypropylamino-3-nitrophenol; HC Yellow No. 13; 1,2,3,4-tetrahydro-6-nitrochinoxalin; HC Red No. 14; HC Yellow No. 15; HC Yellow No. 14; 3-amino-6-methylamino-2-nitropyridine; 2,6-diamino-3-((pyridine-3-yl)azo)pyridine; Basic Red No. 118; Basic Orange No. 69; N-(2-nitro-4-aminophenyl)-allylamine; 4-[(4-amino-3-methylphenyl)(4-imino-3-methyl-2,5-cyclohexadien-1-ylidene) methyl]-2-methyl-benzeneamine-hydrochloride; 2-[[4-(dimethyl-amino)phenyl]azo]-1,3-dimethyl-1H-imidazolium chloride; 1-methyl-4-[(methylphenyl-hydrazono)methyl]-pyridinium, methyl sulfate; 2-[(4-aminophenyl)azo]-1,3-dimethyl-1H-imidazolium chloride; Basic Red 22; Basic Red 76; Basic Brown 16; Basic Yellow 57; 7-(2',4'-dimethyl-5'-sulfophenylazo)-5-sulfo-8-hydroxynaphthalene; Acid Orange 7; Acid Red 33; 1-(3'-nitro-5'-sulfo-6'-oxophenylazo)-oxo-naphthalene chromium complex; Acid Yellow 23; Acid Blue 9; Basic Violet 14; Basic Blue 7; Basic Blue 26; sodium salt of mixture of mono- & disulfonic acids (mainly the latter) of quinophthlanone or 2-quinolylindandione; Basic Red 2; Basic Blue 99; Disperse Red 15; Acid Violet 43; Disperse Violet 1; Acid Blue 62; Pigment Blue 15; Acid Black 132; Basic Yellow 29; Disperse Black 9; 1-(N-methylmorpholinium-propylamino)-4-hydroxy-anthraquinone methylsulfate; N,N-dimethyl-3-((4-(methylamino)-9,10-dioxo-9,10-dihydroanthracen-1-yl) amino)-N-propylpropan-1-aminium bromide, HC Blue No. 8; HC Red No. 8; HC Green No. 1; HC Red No. 9; 2-hydroxy-1,4-naphthoquinone; Acid Blue 199; Acid Blue 25; Acid Red 4; Henna Red; Indigo; Cochenille; HC Blue No. 14; Disperse Blue 23; Disperse Blue 3; Disperse Blue 377; Basic Red 51; Basic Orange 31; Basic Yellow 87; and mixtures thereof. Preferred direct dyes include but are not limited to: Disperse Black 9; HC Yellow 2; HC Yellow 4; HC Yellow 15; 4-nitro-o-phenylenediamine; 2-amino-6-chloro-4-nitrophenol; HC Red 3; Disperse Violet 1; HC Blue 2; Disperse Blue 3; Disperse Blue 377; Basic Red 51; Basic Orange 31; Basic Yellow 87; and mixtures thereof.

To obtain specific color shades, moreover, additional conventional natural and/or synthetic direct dyes can be contained in the colorant, for example plant pigments such as henna or indigo, triphenylmethane dyes, aromatic nitro dyes, azo dyes, quinone dyes, cationic dyes (Basic dyes) or anionic dyes (Acid dyes).

Chelants

The hair colorant compositions or sub-components thereof (such as a tint composition or developer composition) comprise a carboxylic acid chelant, a phosphonic acid chelant, a polyphosphoric acid chelant, salts thereof, or mixtures thereof. Suitable chelants include diethylenetriamine pentaacetic acid (DTPA), ethylenediamine-N,N'-disuccinic acid (EDDS), ethylenediamine-N,N'-diglutaric acid (EDDG), 2-hydroxypropylenediamine-N,N'-disuccinic acid (HP-DDS), glycinamide-N,N'-disuccinic acid (GADS), ethylenediamine-N-N'-bis(ortho-hydroxyphenyl acetic acid) (ED-DHA), diethylene-triamine-penta-(methylenephosphonic acid) (DTPMP), salts thereof, derivatives thereof, or mixtures thereof.

The hair colorant composition or sub-component thereof, such as the tint composition, comprise from about 0.01% to about 5%, from about 0.25% to about 3%, from about 0.5% to about 1% by weight of the hair colorant composition, or sub-component thereof of chelant, salts thereof, derivatives thereof, or mixtures thereof.

Radical Scavenger

The hair colorant compositions, preferably the tint compositions, may further comprise a source of radical scavenger. As used herein the term radical scavenger refers to a species that can react with a carbonate radical to convert the carbonate radical by a series of fast reactions to a less reactive species, i.e. a carbonate radical scavenger.

Suitable radical scavengers for use herein may be selected from the classes of alkanolamines, amino sugars, amino acids, esters of amino acids and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof. Especially preferred compounds are glycine, sarcosine, lysine, serine, 2 methoxyethylamine, glucosamine, glutamic acid, morpholine, piperidine, ethylamine, 3 amino-1-propanol and mixtures thereof.

The compositions of the present invention may comprise from about 0.1% to about 10% by weight, preferably from about 1% to about 7% by weight of the hair colorant composition or the tint composition of a radical scavenger.

Preferably, the radical scavenger is present at an amount such that the weight ratio of radical scavenger to carbonate ion is from 2:1 to 1:4. The radical scavenger is also preferably selected such that it is not an identical species as the alkalizing agent.

Conditioning Agent

The hair colorant composition may comprise a conditioning agent although the conditioning agent would need to be carefully selected to not inhibit foam formation or stabilization, including premature foam collapse. Optionally, a separate conditioning composition comprising a conditioning agent may be used with the hair colorant product.

Conditioning agents suitable are selected from silicone materials, amino silicones, fatty alcohols, polymeric resins, polyol carboxylic acid esters, cationic polymers and mixtures thereof. Additional materials include glycerin and sorbitol. Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain or mixtures thereof. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion.

The conditioning agent may be used at levels of from about 0.05% to about 20% by weight of the conditioning composition, such as from about 0.1% to about 15%, such as of from about 0.2% to about 10%, such as from about 0.2% to about 2% by weight of the conditioning composition. If utilized in the hair colorant composition itself, the conditioning agent may be used from about 0.05% to about 5% by weight of the hair colorant composition.

Other Optional Ingredients

Other ingredients, whether conventionally used in hair colorant compositions or not, may be included if desired and are not adverse to the formation of foam in composition including compositions essential free of surfactant. Hence evaluation of any additional ingredient versus the overall composition functionality is needed and exclusion of components resulting in premature foam collapse, such as oily or greasy substances, is advisable.

Hair Colorant Composition Product

In one embodiment, the present application relates to a hair colorant composition product comprising a manually-actuable, non-aerosol dispenser equipped with a reservoir comprising a reservoir volume, a mixing chamber and a dispensing head. The reservoir may contain an hair colorant composition and when the manually-actuable, non-aerosol dispenser is actuated, the hair colorant composition is mixed with air in a liquid to air ratio of from about 1:6 to about 1:15 and the hair colorant composition is dispensed as a foam.

Manually-actuable, non-aerosol dispensers for foam generation are well known in the art. These foam dispensers comprise a reservoir for holding a liquid to be dispensed in the form of foam with an assembly which can be mounted on or in an opening of the reservoir. The assembly comprises a dip tube which extends into the reservoir and then into a mixing chamber, a liquid pump for pumping the liquid from the reservoir and an air pump to mix air with the liquid in the mixing chamber in order to form foam. The foam is dispensed out of the mixing chamber and through a dispensing channel out of a dispensing head comprising a dispensing orifice. In the dispensing channel one or more porous elements such as sieves or screens that may be arranged to form homogeneous foam.

The amount of work required for dispensing the hair colorant composition with the rheology profiles described herein is unique verses known hair colorant compositions. It is unique in that with known hair colorant compositions, more work is expended moving air than the liquid in such systems. For the hair colorant compositions of the present invention having specific rheology profiles, more work is expended to move the liquid than the air in such systems. The dispensing of the hair colorant composition can be carried out by squeezing an exterior of the reservoir of the manually-actuable, non-aerosol dispenser. Consistent therewith, the foam can be dispensed through the dispensing head orifice of the dispensing head.

The use of hair colorant compositions with the desired rheology profile and the amount of work required to move the hair colorant composition further poses unique problems relating the amount of shear generated in the manually-actuable, non-aerosol dispensers suitable for use herein. The use of hair colorant compositions with the desired rheology profile further affects the ratio of air to liquid. The amount of work, shear generation and air to liquid ratio are aspects that can be attributed to the manually-actuable, non-aerosol dispenser structure.

The ratio of air to liquid is from about 1:6 to about 1:15, preferably from about 1:8 to about 1:12, preferably 1:10.

Suitable manually-actuable, non-aerosol dispenser structure include the dimensions of the dip tube, dimensions of the air ingress into the mixing chamber, mixing chamber dimensions, including the ingress and egress orifices from the mixing chamber, dispensing channel dimensions, porous elements (such as screens or meshes) and dispensing head orifice.

The manually-actuable, non-aerosol dispenser may be exemplified by the following patents: U.S. Pat. No. 3,709,437; U.S. Pat. No. 3,937,364; U.S. Pat. No. 4,022,351; U.S. Pat. No. 4,147,306; U.S. Pat. No. 4,184,615; U.S. Pat. No. 4,615,467; and FR 2,604,622. One particular example of a squeeze foamer useful herein is a squeeze foamer that is able to dispense from an upright or inverted position such as the one discussed in U.S. Pat. No. 6,604,693 assigned to Taplast, and more specifically, at column 2, line 65, through column 4, line 67 of that patent.

The manually-actuable, non-aerosol dispenser may comprise a reservoir. The reservoir comprises a volume such that the reservoir volume is larger that the volume of the hair colorant composition contained within the reservoir. The area of the reservoir that is not occupied by the hair colorant composition is the head space. The head space should remain relatively free of the hair colorant composition or bubbles of the hair colorant composition. If the reservoir is shaken or inverted while the hair colorant composition is contained therein, the head space should remain relatively free of the hair colorant composition or bubbles. As used herein, "relatively free" means less than 50%, such as less than 75%, such as less than 90%, such as 75% to 100% of the head space contains the hair colorant composition or bubbles.

The reservoir is selected to have enough volume to contain the hair colorant composition, any mechanism for foaming the hair colorant composition and head space. The reservoir volume in one embodiment is selected to be from about 100 ml to about 500 ml, from about 150 ml to about 400 ml, such as 250 ml. The ratio of the reservoir volume to hair colorant composition volume is from about 1:0.30 (30% full) to about 1:0.70 (70% full), such as from about 1:0.40 (40% full) to about 1:0.55 (55% full) (i.e., the reservoir volume is larger than the hair colorant composition volume).

The shape of the reservoir may be selected such that when the hair colorant composition is contained within the reservoir, the force required per volume displacement may be optimized. In one embodiment, the force required per volume' displacement is optimized when the shape of the bottle is selected to have an elliptical cross-section as viewed from vertical axis of the bottle (from the top or bottom of the bottle). The elliptical cross-section is preferably concentric such that a neck suitable for a threaded or snap-on cap may be used to close the reservoir. The major axis of the elliptical cross-section is orientated such that it is perpendicular to the force applied to the reservoir surface FIG. 1 illustrates a general structure for a personal care composition product (25) comprising a foamer assembly (1) and a reservoir (3).

The reservoir (3) having a reservoir volume (27) that contains the personal care composition is fluidly connected to the mixing chamber (5) such that the personal care composition is transported from the reservoir (3) when the manually-actuable, non-aerosol dispenser (25) is dispensed (e.g., "stroke"). The fluid connection is a dip tube (7). The dip tube (7) diameter for the present personal care composition having a relatively higher viscosity requires a relatively larger diameter in order to allow for easy dispensing (low amount of force needed to dispense) and to achieve the desired foam specific volume.

The dip tube (7) diameter is preferably selected to have a diameter of greater than 2.0 mm, preferably from about 2.0 mm to about 5.0 mm, more preferably from about 2.5 mm to about 4.0 mm. The viscosity of the liquid with a dip tube (7)

diameter between about 2.0 mm and about 4.0 mm allows for the liquid to be conveyed from the reservoir (3) into the mixing chamber (5) with lower amounts of force by the user during dispensing (e.g., "stroke") while achieving the desired foam density discussed herein.

The mixing chamber (5) comprises at least one air ingress orifice (9), at least one liquid ingress orifice (11) and at least one mixing chamber egress orifice (13). The mixing chamber (5) further comprises an internal volume and an exterior wall, which defines the internal volume of the mixing chamber (5). The mixing chamber (5) allows for the combination of the personal care composition and air to begin the formation of the foamed personal care composition. Modification of the various orifice (9, 11, 13) areas (the two-dimensions of the indicating orifices that comprise part of the mixing chamber (5) exterior wall) can affect the foam specific density, particularly the correlation of the air ingress orifice (9) and the liquid ingress orifice (11) such that the liquid to air ratio is appropriate.

The air ingress orifice (9) is suitable to convey air that has entered into the headspace of the reservoir (3). The mixing chamber (5) may comprise more than one air ingress orifice (9). In one embodiment, the mixing chamber (5) comprises one air ingress orifice (9). The area of the air ingress orifice (9) may be from about 0.62 mm$^2$ (about a 0.2 mm diameter circular air ingress orifice) to about 3.14 mm$^2$ (about a 1 mm diameter circular air ingress orifice), preferably from about 1.26 mm$^2$ (about a 0.4 mm diameter circular air ingress orifice) to about 1.88 mm$^2$ (about a 0.8 mm diameter circular air ingress orifice). If more than one air ingress orifice (9) is selected, the total area of all air ingress orifices (9) should be used. Communication of the air in to the mixing chamber (5) via the air ingress orifice (9) can be and indirect communication with the mixing chamber (5) or a direct communication with the mixing chamber (5).

Similarly, the liquid ingress orifice (11) is suitable to fluidly convey the personal care composition into the mixing chamber (5) from the reservoir (3), preferably via a dip tube (7). In one embodiment, the mixing chamber (5) comprises more than one liquid ingress orifice (11). In one embodiment, the mixing chamber (5) comprises three liquid ingress orifices (11). The area of the liquid ingress orifice (11) should be from about 1.5 mm$^2$ to about 3 mm$^2$. In one embodiment the liquid ingress orifice (11) should be from about 1.8 mm$^2$ to about 2.3 mm$^2$. If more than one liquid ingress orifice (9) is selected, the total area of all air ingress orifices (9) should be used. For example, a total area of 2.0 mm$^2$ for three liquid ingress orifices (11) would equate the total areas of all three liquid ingress orifices (11) combined. The fluid conveyance from the reservoir (3) to the mixing chamber (5) may be an indirect communication pathway with the mixing chamber (5) or a direct communication pathway with the mixing chamber (5).

As used herein "indirect communication" means that the conveyance of the air or personal care composition to the mixing chamber (5) travels along a pathway through some other physical structure before entering into the mixing chamber (5). For example, the air or personal care composition will come into contact with the exterior wall of the mixing chamber (5) before entering into the mixing chamber (5) through the respective orifice (9, 11). In one embodiment, a void volume (30) is contiguous with the exterior wall of the mixing chamber (5). The air or the personal care composition is conveyed from the reservoir, through the dip tube (7) into the void volume (30) external to the mixing chamber (5). The void volume (30) is in air and/or in liquid communication with the air ingress orifice (9) and/or the liquid ingress orifice (11), respectively.

As used herein "direct communication" means that the conveyance of the air or personal care composition to the mixing chamber (5) travels directly into the mixing chamber (5). For example, the air or personal care composition will come into contact with the internal volume of the mixing chamber (5) through the respective orifice (9, 11) without contacting a component exterior to the mixing chamber (5).

In one embodiment, the mixing chamber egress orifice (13) is selected to create an increase in pressure within the mixing chamber (5). The mixing chamber (5) may comprise more than one mixing chamber orifice (13). In one embodiment, the mixing chamber (5) comprises one mixing chamber egress orifice (13).

The mixing chamber (5) has an outer wall creating an internal volume of the mixing chamber (5). The top edge of the outer wall defines a circumference. The mixing chamber egress orifice (13) may be the same size area of the circumference of the mixing chamber (5) top edge, but preferably is selected to be smaller area than the area of the circumference of the mixing chamber (5) top edge so as to create an increase in pressure in the mixing chamber (5). The area of the mixing chamber egress orifice (13) may be between about 0.314 mm$^2$ (0.1 mm diameter circular orifice) to about 9.42 mm$^2$ (3 mm diameter circular orifice). In one embodiment, the mixing chamber egress orifice (13) comprises an area of about 2.512 mm$^2$ (0.8 mm diameter circular orifice) to about 5.652 mm$^2$ (1.8 mm diameter circular orifice). If more than one mixing chamber egress orifice (13) is present, the total area of all of the mixing chamber egress orifices should be considered.

In an embodiment, a diffuser plate (29) comprises the mixing chamber egress orifice (13). The diffuser plate (29) may be part of the mixing chamber (5) structure or it may be a separate component that fits into the mixing chamber (5). It is believed that the diffuser plate (29) helps increase the residence time in the mixing chamber (5) and subjects the personal care composition to more time in the shear generated in the mixing chamber (5).

The mixing chamber (5) is fluidly connected to the foamer assembly (1). The personal care composition enters into the mixing chamber (5) via the liquid ingress orifice (11) and mixes with air which enters the mixing chamber (5) via the air ingress orifice (9).

The air is ordinarily supplied from the environment exterior to the manually-actuable, non-aerosol dispenser (25), the air entering the manually-actuable, non-aerosol dispenser (25) after a stroke which is then located in the headspace of the reservoir (3). The controlled entry or exit of air into the manually-actuable, non-aerosol dispenser (25) reservoir (3) headspace may be accomplished by a ball valve (23) or silicone seal or gasket. The ball valve or silicone seal or gasket may be located in the foamer assembly (1) an in communication with the headspace. In one embodiment, the ball valve (23, silicone seal or gasket is located to communicate between the reservoir (3) and the air external to the manually-actuable, non-aerosol dispenser (25) such that when the manually-actuable, non-aerosol dispenser (25) is being dispensed, the ball valve (23) silicone seal or gasket excludes entry of air external to the manually-actuable, non-aerosol dispenser (25) into the reservoir (3) headspace so that the air in the headspace is conveyed to the mixing chamber through the air ingress orifice (9). After dispensing ("stroke"), the ball valve (23), silicone seal or gasket allows entry of air external to manually-actuable, non-aerosol dispenser (25) to enter into the reservoir (3) to refill the headspace for the next stroke.

After the personal care composition and air enter into the mixing chamber (5) and form the foamed personal care composition, the foamed personal care composition exits the mixing chamber (5) via the mixing chamber egress orifice (13), traveling through a foam fluid connection (17) to the foamer assembly (1) and exits the foamer dispensing orifice (19). The foam fluid connection (17) between the mixing chamber egress orifice (13) and the foamer dispensing orifice (19) may have present therein one or more screens or meshes (21a, 21b, 21c) which may be used to modify the foam specific volume. The number of meshes, the size of the openings in the meshes and the frequency of the openings in the meshes may be used to modify the foam specific volume. In one embodiment, at least 2 meshes (21a, 21b) are utilized, wherein the 2 meshes (21a, 21b) are contiguous with each other. The meshes comprise a diameter section and a depth. The diameter section (largest surface area of the mesh) is the portion of the mesh which would be contiguous with another mesh.

At least a lower portion of the dip tube (7) may be angled toward a lowermost front corner of the reservoir (3) when the reservoir (3) is tilted at an angle for optimal squeezing and dispensing of foam, so as to maximize efficient use of the personal care composition in the reservoir (3). The angle of incline of the lowermost portion of the dip tube (7) preferably mimics the angle of incline of the foamer dispensing orifice (19), and both are preferably at an angle downward from a horizontal axis through the mesh closest to the dispensing head orifice (19) in a range of about 30° to about 45°.

In one embodiment, one to three meshes are present in the fluid connection between the mixing chamber egress and the dispensing head orifice. In one embodiment, two meshes (21a, 21b) are located in the foam fluid connection (17) in close proximity to the mixing chamber egress orifice (13), wherein the two meshes (21a, 21b) comprise about 170 micron (μ) opening size and wherein one mesh (21c) is located in close proximity to the foamer dispensing orifice (19), wherein the one mesh (21c) comprises about a 70 micron (μ) opening size.

In one embodiment two meshes (21a, 21b) located in the foam fluid connection (17) in close proximity to the mixing chamber egress orifice (13) and the two meshes (21a, 21b) are contiguous with each other, wherein the two meshes (21a, 21b) comprise about 170 micron (μ) opening size and wherein one mesh (21c) is located in close proximity to the foamer dispensing orifice (19), wherein the one mesh (21c) comprises about a 70 micron (μ) opening size. Each mesh is preferably provided as an injection molded wafer or disc having a cylindrical sidewall and a screen extending across one end of the cylindrical sidewall. The screen does not extend axially (from the top edge of the cylindrical sidewall to the bottom edge of the cylindrical sidewall moving along the y-axis) the entire length of the cylindrical sidewall. As used in this paragraph, "contiguous" means that the two cylindrical sidewalls of the respective wafers or discs are immediately adjacent one another. However, each of the respective wafers is preferably oriented with its screen is facing up, such that even with the two wafers or discs in contact with one another, there is a gap separating the screen of the first disc from the screen of the second disc.

Turning now to FIG. 3, a particularly preferred embodiment is illustrated in which only two meshes (21a, 21c) are utilized, one (21a) in close proximity to the mixing chamber egress orifice (13) and the other (21c) disposed close proximity to the foamer dispensing orifice (19).

By varying the size of the mixing chamber egress orifice (13), the number of meshes (21a, 21b, 21c), and the opening size of the screens of the meshes, it is possible to reduce the amount of work required to expel a desired quantity of foam, while substantially preserving the desired foam specific volume. For instance, in an exemplary implementation of the embodiment illustrated in FIG. 1, a mixing chamber egress orifice (13) of 1 mm diameter is provided in a diffuser plate (29) [area of orifice is pi*diameter]. In that embodiment, three mesh wafers or discs are provided in the foam fluid connection (17), with each of the first two (21a, 21b) comprising a mesh opening size of about 170 micron (μ), and the third comprising a mesh opening size of about 70 micron (μ).

In an exemplary implementation of the embodiment illustrated in FIG. 3, the second mesh (21b) is omitted, the mixing chamber egress orifice is increased to 1.75 mm in a diffuser plate (29) [area of orifice is pi*diameter], the first mesh (21a) has a mesh opening size of about 170 micron (μ), and the mesh wafer or disc (21c) comprises a mesh opening size of about 70 micron (μ) in located in the foam fluid connection (17).

Kits

The hair colorant composition products may be sold as a kit containing a tint composition component and a developer composition component that are packaged with gloves and instructions. Optionally a conditioning composition component and/or a color referresher composition may also included. A user will combine the tint composition component and developer composition component and then apply the mixed composition in the form of foam to hair.

The tint composition component of the present application may contain at least one hair dye that is selected from oxidative dye precursors, couplers and direct dyes. Additional materials included in the tint composition component include an alkalizing agent, perfume with an Average ClogP of less than 1.5, solvent, radical scavengers and foam stabilizing agents. The tint composition is substantially free of surfactant.

The developer composition component of the present application may contain a solvent, an oxidizing agent and foam stabilizing agents. The developer composition component is substantially free of surfactant.

Generally, the weight ratio of tint formulation:developer formulation is in the range 5:1 to 1:5, such as 1:1, 1:1.5, 1:2, 1:3 and 1.4 depending on strength of developer composition and tint composition.

Included in the kit of the present application is manually-actuable, non-aerosol dispenser. The dispenser is capable of dispensing the mixture of the tint composition component and developer composition component in a foam comprising a specific foam volume from about 6 ml/g to about 14 mL/g, preferably from about 7.5 ml/g to about 12 ml/g, more preferably from about 8 ml/g to about 10.5 ml/g.

The kit may contain two or more containers. In one embodiment, the tint composition component is contained in one container and the developer composition component is contained in the manually-actuable, non-aerosol dispenser or reservoir of the manually-actuable, non-aerosol dispenser.

Optional components for the kit include a conditioner composition and a refreshing color composition. The conditioner composition may comprise a conditioning agent. The refreshing color composition may comprise a conditioning agent and direct dyes.

Method of Use

A user mixes a tint composition and a developer composition together in the reservoir of the manually-actuable, non-aerosol dispenser immediately before use. The user may then shake to mix the tint composition and developer composition. Shaking may be in a vertically reciprocating motion or in a rotating reciprocating shaking motion for a minimum of 10 seconds to mix the tint composition and developer composition. The user then actuates the manually-actuable, non-aerosol dispenser to dispense foam (foamed hair colorant composition) either into the user's gloved hand or directly onto the hair. The foam may begin to collapses between about 10 seconds to 30 minutes after being dispensed. The exemplified compositions given in the tables 7 and 8 hereinafter illustrate suitable compositions.

After allowing the collapsed foam (now a liquid composition) to remain on the hair for 5 to 30 minutes (to ensure uniform application to all of the hair), the user then rinses his/her hair thoroughly with water and allows it to dry.

When present, the optional conditioning agent can be provided in another container. In one embodiment, the content of the conditioner container can be applied (after an optional rinse step) as a post-treatment immediately after the hair colorant composition.

According to the present invention, the methods of coloring hair also comprise embodiments whereby the foamed hair colorant composition of the present invention is applied to the hair and preferably the mixture is worked into the hair by a user's fingers or a comb or similar implement for a few minutes (to ensure uniform application to all of the hair). The composition is then allowed to remain on the hair in order for the color to develop for a time period of less than about 20 minutes, preferably less than about 15 minutes, more preferably from about 5 minutes to about 10 minutes, most preferably for about 10 minutes. The user then rinses his/her hair thoroughly with tap water and allows it to dry and or styles the hair as usual.

According to a further alternative embodiment of the present invention, the method of coloring the hair is a sequential hair coloring method comprising the steps of at least two sequential hair color treatments wherein the time period between each treatment is from 1 to 60 days, preferably from 1 to 40 days, more preferably from 1 to 28 days, even more preferably from 1 to 14 days and most preferably from 1 to 7 days. In such embodiments, the time that the composition is retained on head may be less than about 20 minutes and is preferably less than about 10 minutes and most preferably from about 2 minutes to about 5 minutes.

Test Methods
Viscosity
Sample Preparation

The tint composition and developer composition are combined to make an hair colorant composition. The sample preparation of the hair colorant composition should be as follows:

1. combine, in a 1:1 weight ratio the tint composition and the developer composition in a container from which it can be dispensed. The container should be closed or capped.
2. the closed container is then shaken for 15 seconds.
3. The contents of the closed container poured into a 100 tall container available from FlackTek Inc. is then placed onto a DAC 800 FVZ SpeedMixer from FlackTek Inc. set to 1950 rpm for 10 seconds to draw any bubbles in the out of the sample.
4. Any bubbles or foam on the top of the liquid is decanted.
5. The sample is then measured for viscosity.

Low Shear Viscosity and High Shear Viscosity
The low-shear viscosity and the high shear viscosity, as defined above, is measured via a TA Instruments AR2000 Rheometer having the following geometry:
  40 mm 2° stainless steel cone
  40 mm stainless steel plate
  Standard Size DIN or Conical Concentric Cylinders Using the data analysis program of the TA Instruments AR2000 Rheometer, collected data is then graphed and a point at the beginning of the run is recorded as the low-shear viscosity. Data should be run at least twice to ensure correlation of the recorded data.

The low shear viscosity is measured at $0.01\ s^{-1}$ and the high shear viscosity is measured at $500\ s^{-1}$.

Foam Specific Volume

Foam specific volume is measured by placing a 100 ml beaker onto a mass balance, tarring the mass of the beaker and then dispensing from a foaming dispenser into the 100 ml beaker until the volume of the foam is equal to 100 ml. Record the resulting mass of the 100 ml of foam at 5 seconds from the end of dispensing. Dividing the volume (100) by the mass of the foam results in the foam specific volume having the units of mL/g.

Perfume Examples

TABLE 4

Comparative perfume composition with Average ClogP greater than 1.5

| Chemical Name | Amount | LogP (v3.0) | Average Clog P |
|---|---|---|---|
| Ethyl Acetate | 5.000 | 0.39 | 0.020 |
| cis-3-Hexen-1-ol | 1.000 | 1.3 | 0.013 |
| Phenethyl alcohol | 5.000 | 1.44 | 0.072 |
| Heliotropin | 0.100 | 1.12 | 0.001 |
| Ethyl vanillin | 0.100 | 1.51 | 0.002 |
| Benzyl acetate | 4.000 | 1.68 | 0.067 |
| Ethyl 2-methylbutyrate | 1.000 | 2.00 | 0.020 |
| Geraniol | 10.000 | 1.95 | 0.195 |
| Linalool | 5.000 | 2.44 | 0.122 |
| Hexahydro-4,7-methanoinden-5(6)-yl propionate | 1.000 | 2.95 | 0.030 |
| Methyl 2-(2-pentyl-3-oxocyclopentyl-1)acetate | 5.000 | 3.01 | 0.151 |
| Allyl Caproate | 1.800 | 3.03 | 0.055 |
| Dihydro Myrcenol | 5.000 | 3.08 | 0.154 |
| Gamma Decalactone | 1.000 | 3.23 | 0.032 |
| Undecalactone | 1.000 | 3.75 | 0.038 |
| 2-tert.Butylcyclohexyl acetate | 20.000 | 3.87 | 0.774 |
| p-tert.Butyl-alpha-methyldihydrocinnamic aldehyde | 5.000 | 3.88 | 0.194 |
| Ionone Gamma Methyl | 10.000 | 4.01 | 0.401 |
| Dimethyl Benzyl Carbinyl Butyrate | 1.000 | 4.09 | 0.041 |
| Pentadec-11(12)-enolide | 5.000 | 4.32 | 0.216 |
| Hexyl Salicylate | 5.000 | 4.58 | 0.229 |
| 3-Acetyl-3,4,10,10-tetramethylbicyclo[4.4.0]decane | 8.000 | 4.93 | 0.394 |
| Total | 100.000 | | |
| ClogP | | | 3.219 |

The perfume composition of Table 4 used in a hair colorant composition such as those in Table 8 will not result in a foam when passed through a foamer such as that shown in FIG. 1. Examples of suitable perfume include:

TABLE 5

Example 1

| Chemical name | Amt wt %* | ClogP | average Clog P |
|---|---|---|---|
| ethyl maltol | 10 | 0.29 | 0.029 |
| Ethyl 2-methyl-1,3-dioxolane-2-acetate | 38 | 0.92 | 0.3496 |
| Heliotropin | 10 | 1.12 | 0.112 |
| cis-3-Hexen-1-ol | 10 | 1.3 | 0.13 |

TABLE 5-continued

Example 1

| Chemical name | Amt wt %* | ClogP | average Clog P |
|---|---|---|---|
| Phenethyl alcohol | 20 | 1.44 | 0.28 |
| Ethyl vanillin | 5 | 1.51 | 0.0755 |
| Ethyl 2-methylbutyrate | 5 | 2 | 0.1 |
| 2-Butanone,_4-phenyl- | 2 | 2.14 | 0.0428 |
| Total | 100 | | |

*by weight of the perfume composition

Which gives an Average ClogP of 1.127.

TABLE 6

Example 2

| Chemical name | Amt wt %* | ClogP | average Clog P |
|---|---|---|---|
| Ethyl 2-methyl-1,3-dioxolane-2-acetate | 27.0 | 0.92 | 0.248 |
| Heliotropin | 5.0 | 1.12 | 0.056 |
| cis-3-Hexen-1-ol | 5.0 | 1.3 | 0.065 |
| Oxalone | 5.0 | 1.31 | 0.065 |
| p-Anisaldehyde | 2.0 | 1.37 | 0.0274 |
| Phenethyl alcohol | 26.0 | 1.44 | 0.3744 |
| ACETOPHENONE | 7.0 | 1.57 | 0.1099 |
| Benzyl acetate | 2.0 | 1.68 | 0.0366 |
| Florol | 19.0 | 1.95 | 0.3705 |
| Ethyl 2-methylbutyrate | 1.0 | 2 | 0.02 |
| 4,4a,5,9b-tetrahydroindeno[1,2-d]-1,3-dioxin | 1.0 | 2.04 | 0.0204 |
| Total | 100.0 | | |

*by weight of the perfume composition

Which gives an Average ClogP of 1.391.

TABLE 7

Example 3

| Chemical name | Amt wt %* | ClogP | average Clog P |
|---|---|---|---|
| Ethyl Maltol | 12 | 0.29 | 0.0348 |
| Ethyl acetate | 10 | 0.39 | 0.039 |
| Ethyl 2-methyl-1,3-dioxolane-2-acetate | 30 | 0.92 | 0.276 |
| Heliotropin | 10 | 1.12 | 0.112 |
| cis-3-Hexen-1-ol | 5 | 1.30 | 0.065 |
| Phenethyl alcohol | 20 | 1.44 | 0.288 |
| Ethyl vanillin | 5 | 1.51 | 0.0755 |
| Benzyl acetate | 2 | 1.68 | 0.0336 |
| Ethyl 2-methylbutyrate | 1 | 2.00 | 0.02 |
| Amyl-acetate (isomer blend) | 5 | 1.94 | 0.09675 |
| Amyl-acetate (isomer blend) | | | |
| n-Pentyl acetate | 1.50 | 2.11 | 0.633 |
| 2-methyl butyl acetate | <0.1 | | 0 |
| Iso amyl acetate | 3.5 | 1.86 | 1.302 |
| | | average ClogP of isomer blend | 1.94 |

*by weight of the perfume composition

Wherein the amyl-acetate isomer blend is calculated to fine the average ClogP of the isomer blend which is used to find the Average ClogP of 1.04.

Formulation Examples

TABLE 8

Tint Compositions

| Ingredient | Light Blonde Tint % by wt | Medium Gold Brown Tint % by wt | Black Tint % by wt | Red Tint % by wt |
|---|---|---|---|---|
| propylene glycol | 14 | 14 | 14 | 14 |
| ethoxydiglycol | 7 | 7 | 7 | 7 |
| Perfume* | 0.75 | 0.75 | 0.75 | 0.75 |
| disuccinate | 3.35 | 3.35 | 3.35 | 3.35 |
| citric acid (local # 01057820) | 0.4 | 0.4 | | 0.4 |
| isopropyl alcohol | 5 | 5 | 5 | 5 |
| ammonium hydroxide (30%) | 8.25 | 7.5 | 5 | 5 |
| sodium sulfite | 0.1 | 0.1 | 0.1 | 0.1 |
| EDTA (local # 01057577) | 0.05 | 0.05 | 0.05 | 0.05 |
| Sodium Chloride | 1.954 | 1.38 | 0.32 | 0.85 |
| erythorbic acid | 0.4 | 0.4 | 0.4 | 0.4 |
| m-aminophenol (dye) | 0.013 | 0.0093 | 0.6 | — |
| 1-naphthol (dye) | 0.026 | 0.0642 | — | — |
| toluene-2,5-diamine sulphate (dye) | 0.21 | 1.536 | 3.84 | 0.35 |
| n,n-bis(2-hydroxyethyl)-p-phenylenediamine sulphate (dye) | — | 0.0212 | — | — |
| resorcinol (dye) | 0.044 | 0.082 | 1.1 | — |
| p-aminophenol (dye) | 0.015 | 0.223 | — | — |
| 2-methylresorcinol (dye) | 0.197 | 0.385 | — | — |
| 4-amino-2-hydroxytoluene (dye) | — | 0.0093 | — | 1.76 |
| 1-hydroxyethyl 4,5-diamino pyrazole sulphate (dye) | — | — | 0.08 | 2.5 |
| phenyl methyl pryazolone (dye) | 0.05 | 0.1 | 0.1 | 0.1 |
| 2,4-Diaminophenoxyethanol HCl | — | — | 0.7 | — |
| 5-EthylOAP | — | 0.0132 | — | — |
| water | to 100% | to 100% | to 100% | to 100% |

*Perfume may be any one of Ex. 1-3

TABLE 9

Developer Composition

| Ingredient | % by weight of developer composition | % by weight of developer composition | % by weight of developer composition | % by weight of developer composition | % by weight of developer composition |
|---|---|---|---|---|---|
| EDTA disodium dihydrate | 0.04 | 0.04 | 0.04 | 0.04 | 0.04 |
| Etidronic acid | 0.08 | 0.08 | 0.08 | 0.08 | 0.08 |
| Hydrogen peroxide (50% active) | 18.45 | 18.45 | 18.45 | 18.45 | 18.45 |
| ACULYN® 33 | 10.5 | 8.0 | 7.0 | 5.5 | 2.0 |
| ACULYN® 22 | 2.92 | 5.5 | 6.5 | 8.0 | 10.0 |
| water | to 100% | to 100% | to 100% | to 100% | to 100% |

Each tint formulation may be admixed with the developer formulation to provide a hair colorant composition. The weight ratio of tint formulation to developer formulation may be varied depending upon the precise shade required and the degree of bleaching necessary to attain the desired shade. Generally, the weight ratio of tint formulation:developer formulation is in the range 5:1 to 1:5, such as 1:1, 1:2 and 1:3 depending on strength of developer composition and tint composition.

A tint compositions of Table 8 and the developer compositions of Table 9 ware mixed in a 1:1 weight ratio to form an hair colorant composition of the invention. The hair colorant composition is introduced into the container of a squeeze foamer such as that shown in FIG. 1. The device is squeezed and the hair colorant composition is dispensed as foam of acceptable quality.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair colorant product comprising an hair colorant composition contained in a manually-actuable, non-aerosol dispenser, the composition comprising a hair dye, an alkalizing agent, an oxidizing agent, a foam stabilizing agent which is a member selected from the group consisting of polymeric emulsifiers and polymeric foam stabilizers and mixtures thereof and a perfume, the perfume comprising an Average ClogP less than 1.5, wherein the hair colorant composition is substantially free of surfactant and when dispensed from the manually-actuable, non-aerosol dispenser result is a foam comprising a specific foam volume from about 6 ml/g to about 14 ml/g.

2. The hair colorant product of claim 1 wherein the perfume comprises a plurality of perfume raw materials having individual ClogP values in the range of 1.5 to 2.5.

3. The hair colorant product of claim 1 wherein the perfume comprises ethyl 2-methyl-1,3 dioxolane-2-acetate, phenethyl alcohol, heliotropin, cis-3-hexen-1-ol, ethyl 2-methylbutyrate and mixtures thereof.

4. The hair colorant product of claim 3 wherein the perfume further comprises ethyl vanillin, ethyl maltol, benzyl acetate and mixtures thereof.

5. The hair colorant product of claim 1 wherein the perfume comprises less than 500 ppm of contaminates.

6. The hair colorant product of claim 1 wherein the foam stabilizing agent is selected from hydroxypropyl methylcellulose, methylcellulose, cecetyl hydroxyethylcellulose and mixtures thereof.

7. The hair colorant product of claim 1 wherein the foam stabilizing agent is a hydrophobically-modified alkali soluble emulsion polymer having an acid/acrylate copolymer backbone and a monomer that connects the hydrophobic groups as side chains or an anionic alkali-soluble polymer emulsion synthesized from acid and acrylate comonomers or a mixture thereof.

8. The hair colorant product of claim 1 wherein the foam stabilizing agent is selected as an acrylate/$C_{10-30}$ alkyl acrylate crosspolymer.

9. The hair colorant product of claim 1 wherein the foam stabilizing agent is selected as a polymer comprising vinyl pyrrolidone (VP), dimethylaminopropyl methacrylamide (DMAPA) and methacryoylaminopropyl lauryldimonium chloride (MAPLAC).

10. The hair colorant product of claim 1 wherein the foam stabilizing agent is present in an amount in the range from about 4 to about 25% by weight of the composition.

11. The hair colorant product of claim 1 wherein the hair colorant composition comprises less than 200 ppm based on the hair colorant composition of surfactant.

12. The hair colorant product of claim 1 wherein the hair colorant composition comprises a pH between 9 and 11.

13. The hair colorant product of claim 1 wherein said oxidizing agent is a member selected from the group consisting of hydrogen peroxide, percarbonates, perphosphates and mixtures thereof.

14. The hair colorant product of claim 1 wherein the alkalizing agent is selected from ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof.

15. A hair colorant composition comprising:
  (i) a hair dye,
  (ii) an alkalizing agent,
  (iii) an oxidizing agent,
  (iv) a foam stabilizing agent which is a member selected from the group consisting of polymeric emulsifiers and polymeric foam stabilizers and mixtures thereof; and
  (v) a perfume comprising a blend of perfume raw materials in which up to 30% by weight of the perfume consists essentially of perfume raw materials having a ClogP in the range 1.5 to 2.5 and the balance of the perfume consists essentially of perfume raw materials having a ClogP of less than 1.5,
wherein the hair colorant composition is substantially free of surfactant.

16. The hair colorant composition of claim 15 wherein the perfume comprises an Average ClogP less than 1.5.

17. The hair colorant composition of claim 15 wherein the perfume comprises ethyl 2-methyl-1,3 dioxolane-2-acetate, phenethyl alcohol, heliotropin, cis-3-hexen-1-ol, ethyl 2-methylbutyrate and mixtures thereof.

18. The hair colorant composition of claim 17 wherein the perfume further comprises ethyl vanillin, ethyl maltol, benzyl acetate and mixtures thereof.

19. The hair colorant composition of claim 15 wherein the perfume comprises less than 500 ppm of contaminates.

20. A kit comprising containing components to form an hair colorant composition the kit comprising:
  A tint composition component comprising a hair dye, an alkalizing agent and a perfume; wherein the perfume comprises an Average ClogP less than 1.5;
  A developer composition component comprising an oxidizing agent and a foam stabilizing agent which is a member selected from the group consisting of polymeric emulsifiers and polymeric foam stabilizers and mixtures thereof;
  A manually-actuable, non-aerosol dispenser, the dispenser capable of dispending the mixture of the tint composition component and developer composition component in a foam comprising a specific foam volume from about 6 to about 14 ml/g;

Wherein the tint composition component and the developer composition component are essentially free of surfactant.

21. The kit of claim 20 wherein the tint composition comprises a perfume wherein the perfume comprises a plurality of perfume raw materials having individual ClogP values in the range of 1.5 to 2.5.

22. The kit of claim 20 wherein the tint composition comprises a perfume wherein the perfume comprises ethyl 2-methyl-1,3 dioxolane-2-acetate, phenethyl alcohol, heliotropin, cis-3-hexen-1-ol, ethyl 2-methylbutyrate and mixtures thereof.

23. The kit of claim 22 wherein the perfume further comprises ethyl vanillin, ethyl maltol, benzyl acetate and mixtures thereof.

24. The kit of claim 22 wherein the perfume comprises less than 500 ppm of contaminates.

25. The kit of claim 22 wherein said foam stabilizing agent is selected as an acrylate/$C_{10-30}$ alkyl acrylate crosspolymer.

26. The kit of claim 22 wherein said foam stabilizing agent is present in an amount in the range from about 4 to about 25% by weight of the composition.

27. The kit of claim 22 wherein the tint composition comprises less than 200 ppm based on the tint composition of surfactant.

28. The kit of claim 22 wherein the developer composition comprises less than 200 ppm based on the developer composition of surfactant.

29. The kit of claim 22 wherein the developer composition comprises an oxidizing agent selected from the group consisting of hydrogen peroxide, percarbonates, perphosphates and mixtures thereof.

30. The kit of claim 22 wherein the tint composition comprises an alkalizing agent selected from ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof.

31. The kit of claim 22 wherein the manually-actuable, non-aerosol dispenser is equipped with a reservoir comprising a reservoir volume, a mixing chamber and a dispensing head, wherein the reservoir is capable of containing the hair colorant product wherein when the manually-actuable, non-aerosol dispenser is actuated the hair colorant product is mixed with air and is dispensed as a foam.

32. The kit of claim 31 wherein the mixing chamber comprises at least one liquid ingress orifice, a foam egress orifice and an air ingress orifice.

33. The kit of claim 32 wherein air is introduced into the mixing chamber by the air ingress orifice such that the ratio of air to the hair colorant composition is from about 1:6 to about 1:15.

34. The kit of claim 31 wherein the dispenser further comprises a dip tube in the reservoir and connected to the ingress orifice of the mixing chamber, wherein the dip tube has a diameter of greater than 2.0 mm.

* * * * *